United States Patent [19]

Forster et al.

[11] Patent Number: 4,627,269

[45] Date of Patent: Dec. 9, 1986

[54] METHOD OF, AND APPARATUS FOR, DETECTING REDUCING GASES IN A GAS MIXTURE

[75] Inventors: Martin Forster, Jona; Sigfrid Strässler, Baden-Dättwil, both of Switzerland

[73] Assignee: Cerberus AG, Männedorf, Switzerland

[21] Appl. No.: 712,682

[22] Filed: Mar. 18, 1985

[30] Foreign Application Priority Data

Apr. 4, 1984 [CH] Switzerland .................... 1699/84

[51] Int. Cl.⁴ ............................................. G01N 27/12
[52] U.S. Cl. ............................................. 73/23; 73/1 G
[58] Field of Search ................... 73/23, 27 R, 1 G; 340/634; 422/98

[56] References Cited

U.S. PATENT DOCUMENTS

| 3,180,132 | 4/1965 | Robinson et al. | 73/1 G |
| 4,399,684 | 8/1983 | Advani et al. | 73/23 |
| 4,446,718 | 5/1984 | Bukowiecki et al. | 73/23 |

FOREIGN PATENT DOCUMENTS 0092068 10/1983 European Pat. Off. .
1017384 10/1957 Fed. Rep. of Germany .
2313413 3/1973 Fed. Rep. of Germany .

Primary Examiner—Stephen A. Kreitman
Attorney, Agent, or Firm—Werner W. Kleeman

[57] ABSTRACT

Reducing gases can be detected in a gas mixture to be investigated, particularly in air, with high sensitivity and precision by means of a gas detector. The gas detector comprises a gas sensor which is arranged within a measuring chamber. The temperature of the gas sensor can be continuously increased according to a predetermined pattern from a starting value to an upper threshold value and can be subsequently decreased again to the starting value according to the same or according to a different pattern. There are provided at least two such heating cycles. Simultaneously therewith the gas mixture to be investigated, which is present in the measuring chamber, is periodically exchanged against a pure reference gas which is contained in a reference chamber. A selected property, such as the electrical conductivity of the gas sensor is thereby periodically changed. The temporal variation of this periodically varying electric conductivity can be detected in an evaluation circuit arrangement and/or evaluated for determining the concentration and/or the nature of the reducing gases which are present in the gas mixture to be investigated.

121 Claims, 28 Drawing Figures

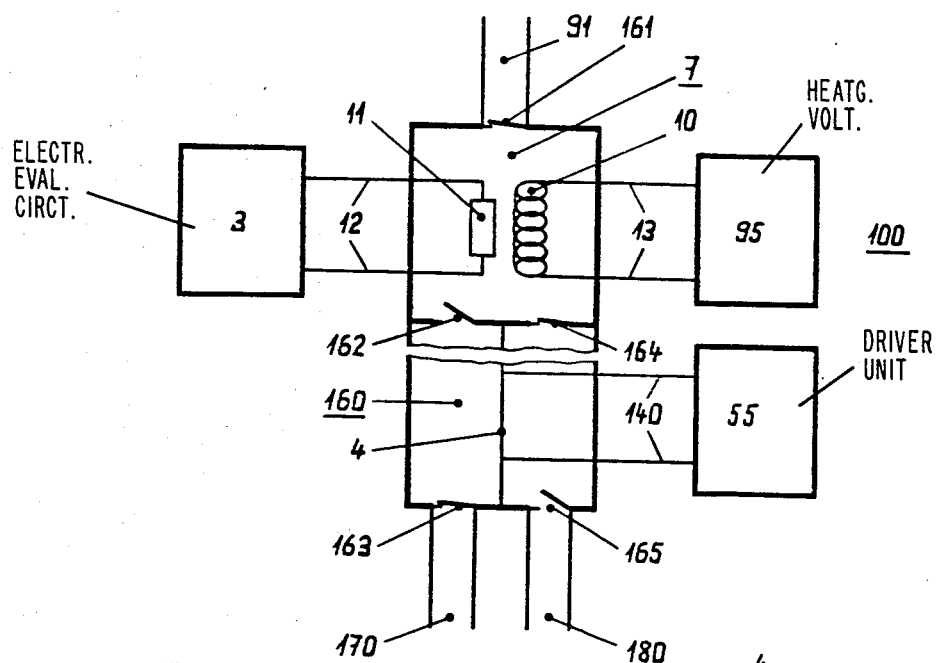
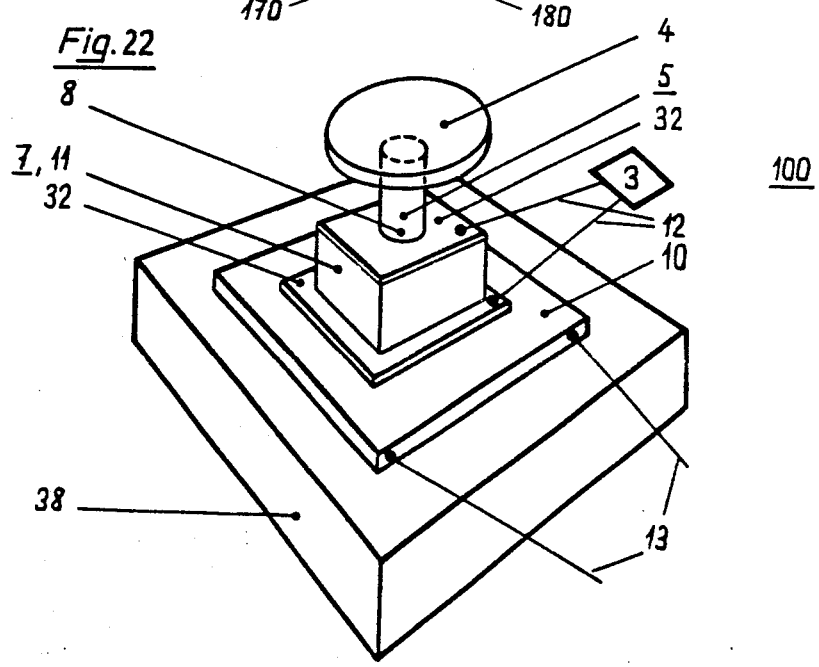

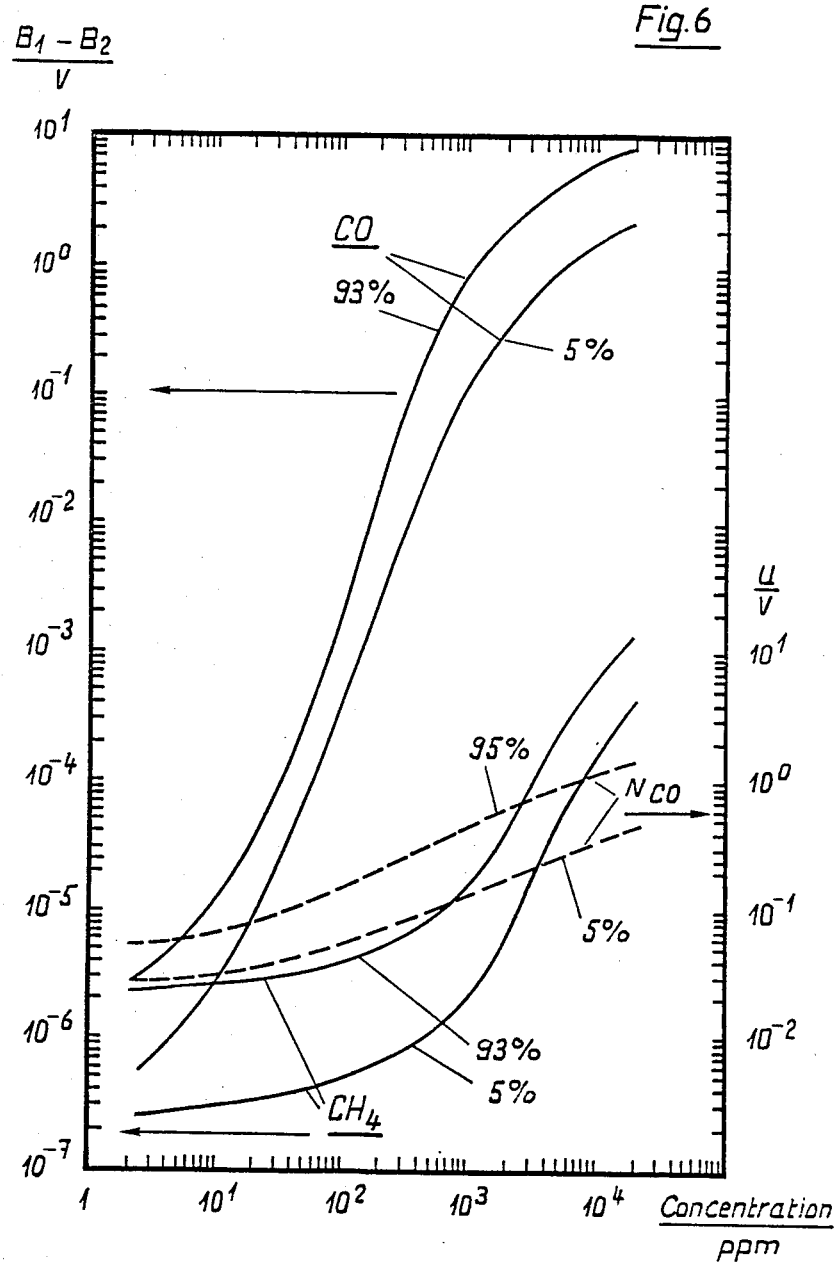

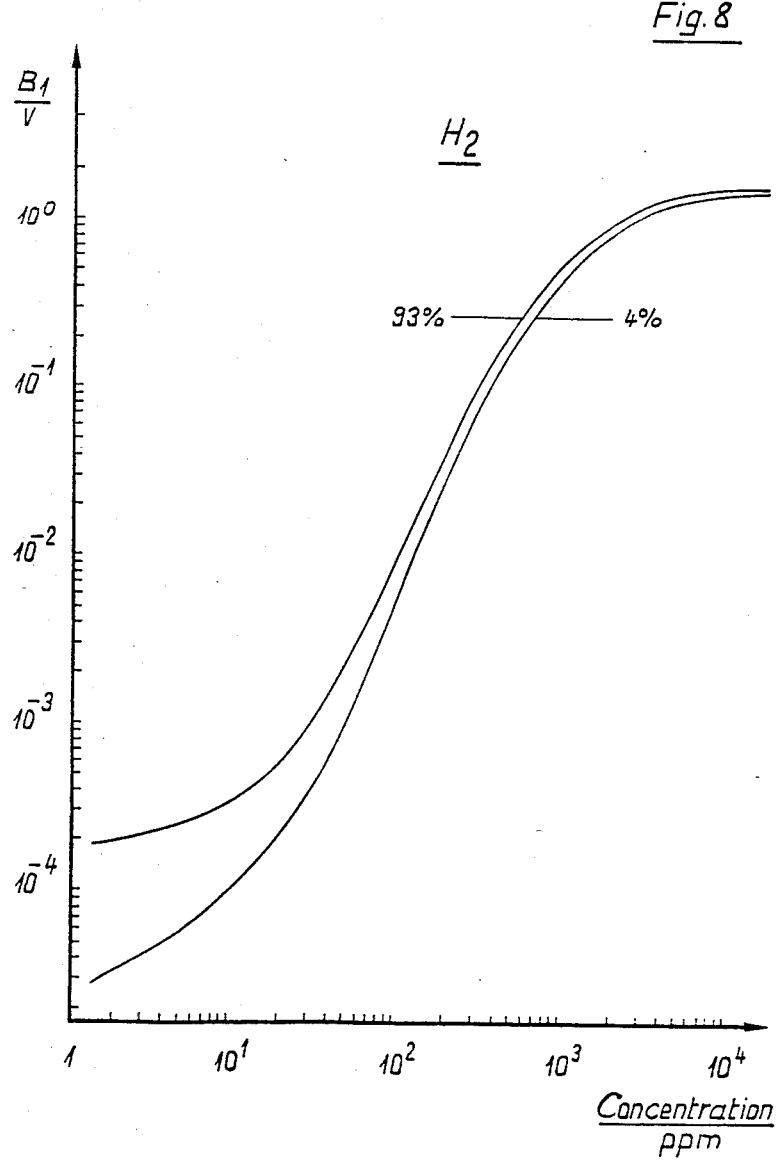

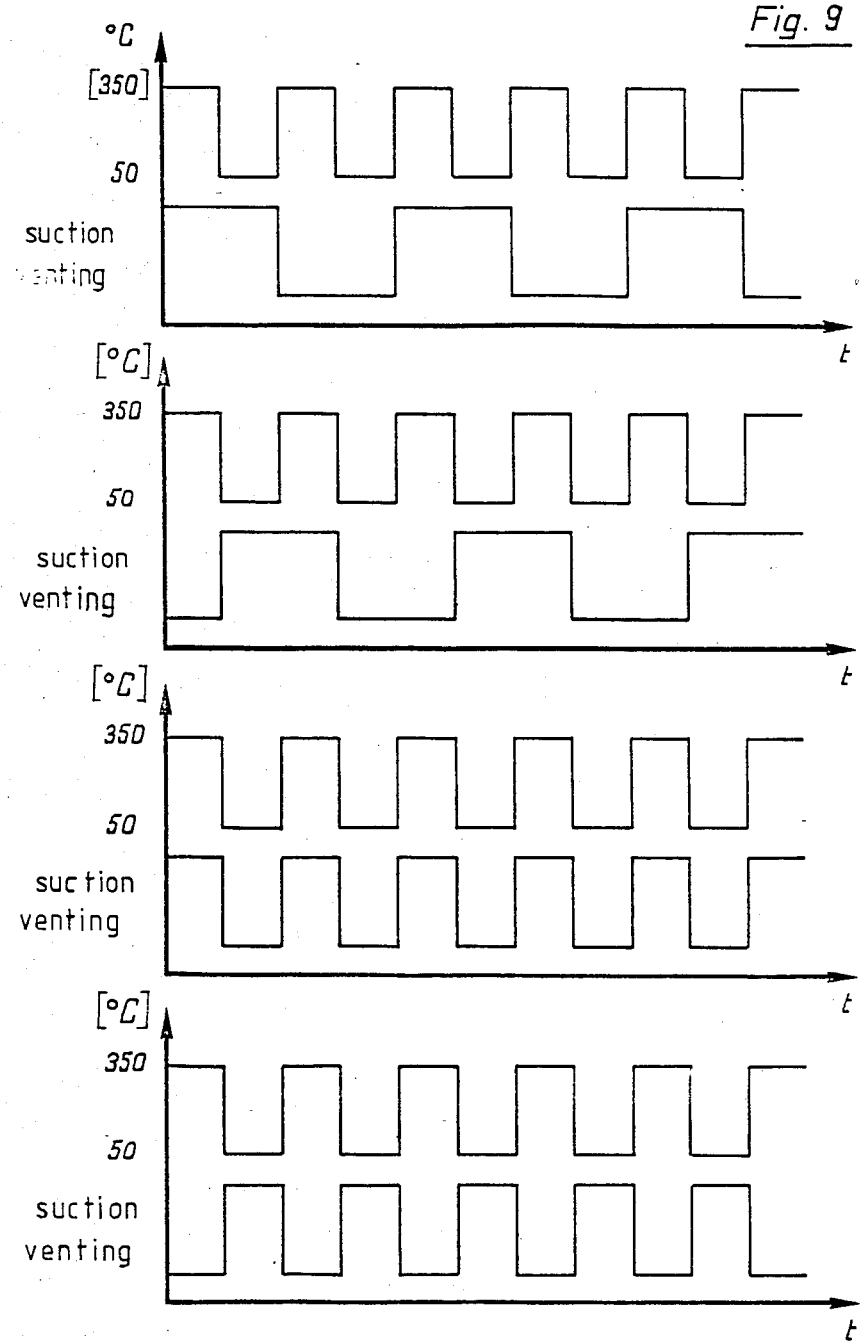

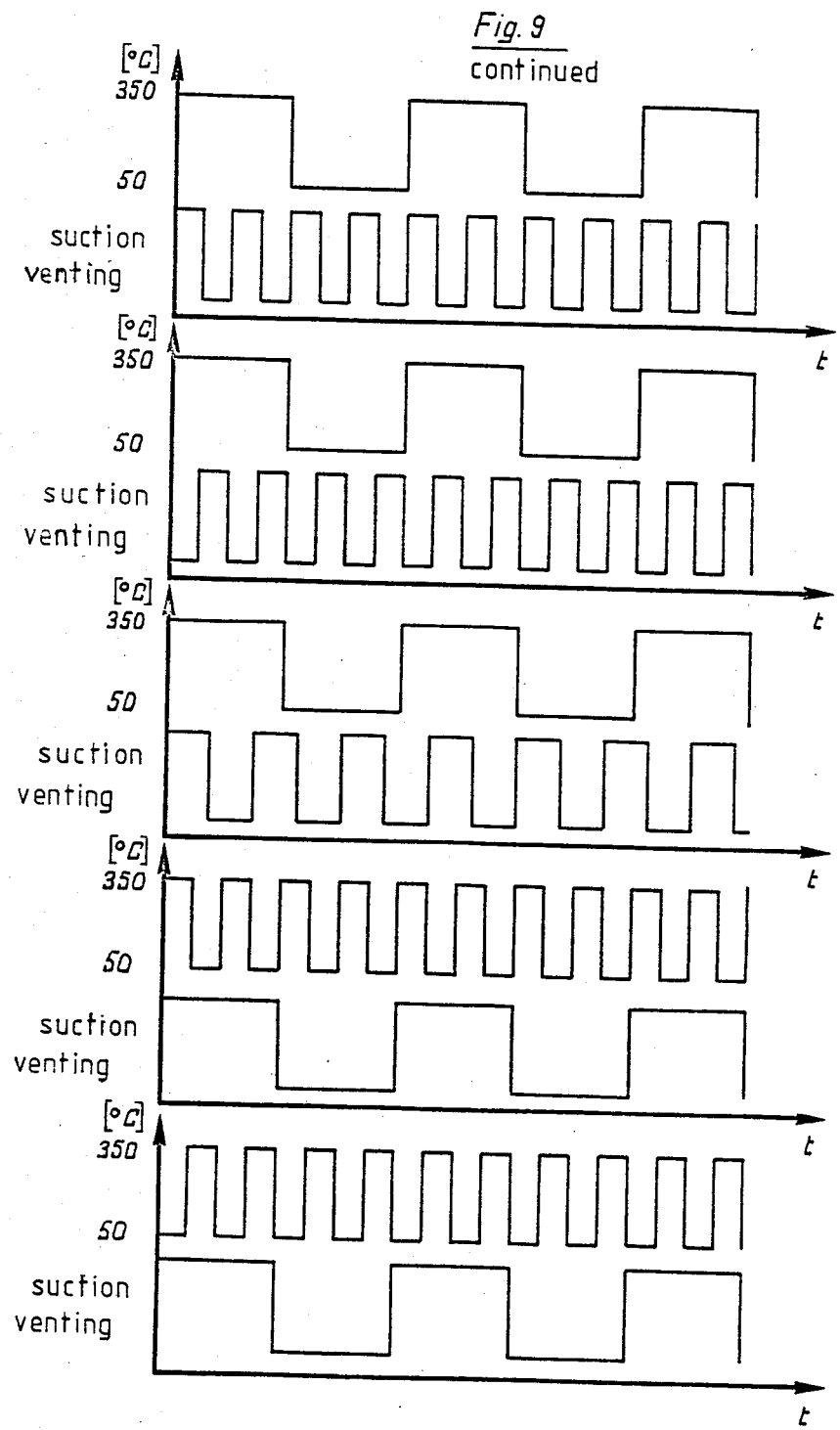

Basic Shapes
*Fig. 10*
 Rectangular
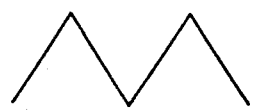 Triangular
 Symmetric Trapezoidal
 Non-symmetric Trapezoidal 
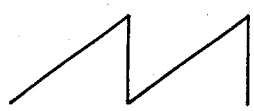 Sawtooth 
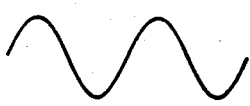 Sinusoidal
 Rectangular through low-pass 
Combination Shapes
 Triangular + Rectangular through low-pass 

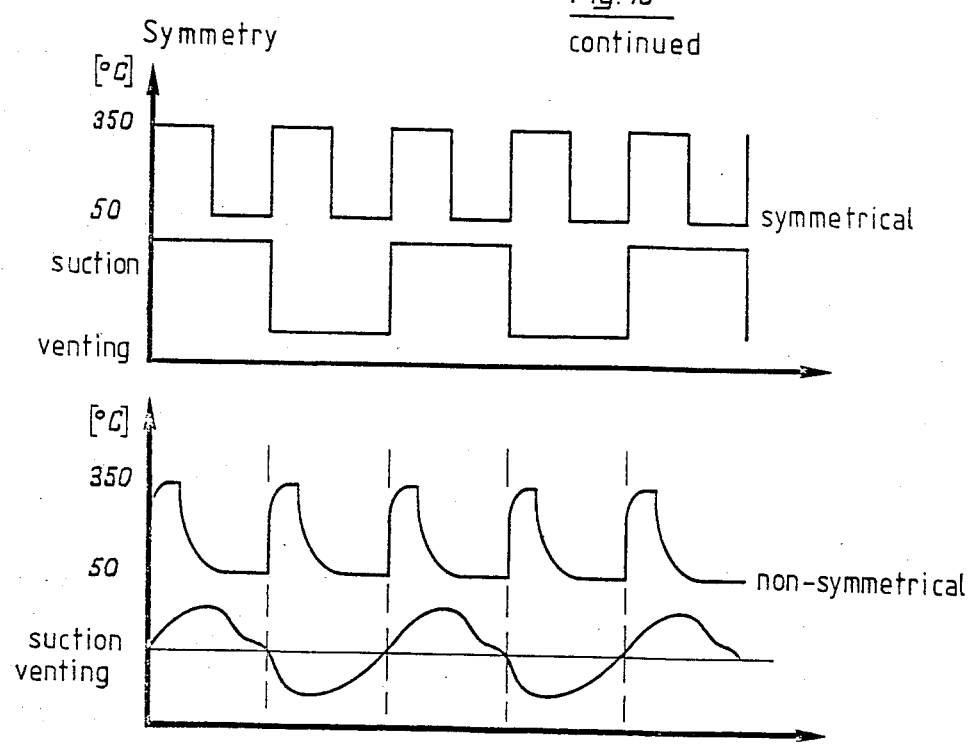

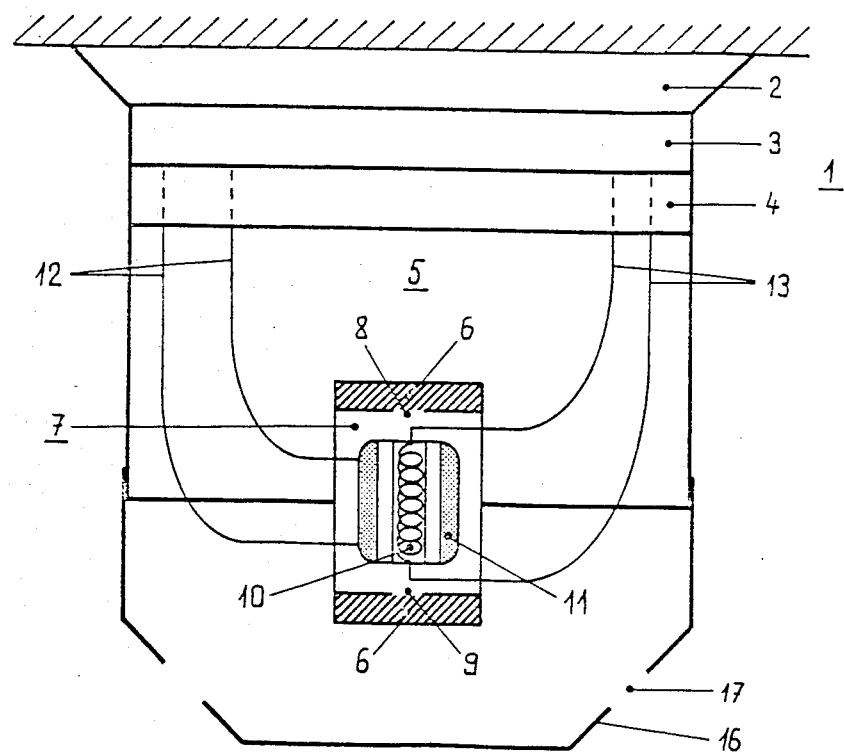

METHOD OF, AND APPARATUS FOR, DETECTING REDUCING GASES IN A GAS MIXTURE

CROSS-REFERENCES TO RELATED APPLICATIONS

This application is related to (i) the commonly assigned, copending U.S. application Ser. No. 06/633,652, filed July 23, 1984, now U.S. Pat. No. 4,579,751, entitled METHOD OF PRODUCING CONSTITUENT MATERIALS FOR GAS SENSORS; (ii) the commonly assigned, copending U.S. application Ser. No. 06/635,881, filed July 30, 1984, entitled DEVICE FOR DETECTING GASEOUS CONTAMINANTS IN AIR BY MEANS OF A GAS SENSOR AND METHOD OF PRODUCING SUCH GAS SENSOR; (iii) the commonly assigned, copending U.S. application Ser. No. 06/640,125, filed Aug. 3, 1984, now U.S. Pat. No. 4,584,867, entitled DEVICE FOR SELECTIVELY DETERMINING THE COMPONENTS OF GAS MIXTURES BY MEANS OF A GAS SENSOR; (iv) the commonly assigned, copending U.S. application Ser. No. 713,274, filed Mar. 18, 1985, entitled METHOD OF, AND APPARATUS FOR, DETECTING REACTIVE GASES IN A GAS MIXTURE; and the commonly assigned, copending U.S. application Ser. No. 713,411, filed Mar. 18, 1985, entitled METHOD OF, AND APPARATUS FOR, DETECTING REDUCING GASES IN A GAS MIXTURE. The disclosures of these applications are incorporated herein by reference.

BACKGROUND OF THE INVENTION

The present invention relates to a new and improved method of, and apparatus for, detecting at least one reducing gas in a gas mixture to be investigated, particularly in air.

In its more particular aspects, the present invention relates specifically to a new and improved method of detecting at least one reducing gas in a gas mixture to be investigated, particularly in air, by means of a gas detector which contains a gas sensor comprising a metal oxide semiconductor. A selected property, such as the electrical conductivity of the gas sensor depends directly upon the concentration of the at least one reducing gas. The temperature of the gas sensor is continuously increased according to a predetermined pattern from a starting value to an upper threshold value and is subsequently decreased again to the starting value according to the same or a different pattern. The gas sensor is subjected to at least two such heating cycles. An electrical output signal of the gas sensor is evaluated in an evaluation circuit arrangement.

In such a method as known, for example, from European Patent Publication No. 0,092,068, published Oct. 26, 1983, a sensor element which is responsive to gases, is subjected to at least two temperature cycles according to a predetermined pattern which is optimized for predetermined gases. In each such temperature or heating cycle the sensor element is continuously heated from a starting value to an upper value and subsequently the temperature is lowered again to the starting value according to the same or according to a different pattern. An evaluation circuit arrangement compares the signal supplied by the sensor element during the temperature or heating cycles. The signal delivered by the sensor element is dependent upon the composition of the gas or vapor atmosphere and the delivered signal is compared with stored values which are characteristic for the presence of predetermined gas and/or vapor components.

By using such method it is possible to fully utilize the broad-band sensitivity range of gas sensors based on metal oxides and to simultaneously and selectively detect individual gases. During the use of such metal oxide semiconductor gas sensors in gas monitoring installations it is required to detect toxic or explosive gases in concentration ranges which are as far as possible below the lower explosion limit. Therefore, there is still a need for methods by means of which trace quantities of explosive gases can be detected.

In a further method as known, for example, from German Patent Publication No. 2,313,413, published Sept. 26, 1974, the carbon monoxide and/or the methane content of a gas mixture present in underground operations is determined by means of measuring the electrical resistance of a metal oxide semiconductor which adsorbs the gas component to be measured and desorbs such component in an accelerated manner at higher temperatures. Prior to each measurement the temperature of the metal oxide semiconductor is varied from a lower threshold value to a higher threshold value and the measurement is conducted at the lower threshold value. The variation of the electrical resistance is measured through a predetermined time interval and the concentration of carbon monoxide and/or methane is determined from the absolute measured value and/or from the variation in time of the measuring signal.

The method described in the aforementioned '413 German patent publication is adapted to the requirements of the mining industry. It has the advantage that a good long-term stability is achieved by periodically heating the metal oxide semiconductor. For detecting carbon monoxide there is required a second measuring chamber which contains a continuously heated metal oxide semiconductor in order to compensate for the interfering sensitivity towards methane-type components. The regeneration of the metal oxide semiconductor between the individual measuring periods requires about 1 to 5 minutes. Subsequently, the metal oxide semiconductor is required to be cooled to room temperature before the actual measuring operation can be started. Such method is therefor unsuited for use in alarm installations in which a rapid recognition of a dangerous concentration of combustible gases is required. Furthermore, the known method is not particularly sensitive because the absolute measured value or the variation of the measuring signal with time is utilized for determining the gas concentration.

A carbon monoxide detector as known, for example, from German Patent Publication No. 2,832,828, contains two carbon monoxide detectors of different sensitivities for reducing the influence of other gases which are simultaneously present in a gas sample. The different sensitivities against carbon monoxide are obtained by different structures of the metal oxide semiconductors which are contained in the carbon monoxide detectors or by different temperatures of the detector elements. Such principle is ineffective for other gases.

In the Japanese Patent Publication No. Sho 49-11997 there is described a gas and smoke detector which comprises two measuring chambers which contain metal oxide semiconductor sensors and which are differently accessible for the air to be investigated in order to suppress the sensitivity towards slow changes in the air properties like, for example, temperature and humidity. The difference of the measuring signals obtained from the two sensors is utilized for evaluation. Due to the ready diffusion, particularly of low-molecular gases the difference between the two measuring signals soon again becomes zero, so that such detector would be rather suited for smoke detection.

In a method for detecting combustible gases as known, for example, from German Pat. No. 1,017,384, granted Oct. 10, 1957, the detection is based on a catalytic combustion of the gases to be detected at a platinum filament and the variation of the resistance thereof is used as the measured magnitude. In this process the platinum filament alternatingly serves as the combustion mass and as a comparison mass by alternatingly passing the gas mixture to be investigated over the platinum filament and a reference gas which contains none or only a small content of the combustible components. The temperature of the platinum filament varies in time between a maximum value corresponding to the combustion period and a minimum value corresponding to a reference gas which contains no combustible components. The evaluation of such temperature variations or fluctuations results in an a.c.-voltage signal, the frequency of which is dependent upon the gas exchange period and the amplitude of which is dependent upon the content of combustible components. The amplitude is then utilized for determining the content of combustible gases.

Using the aforementioned method there can be avoided one disadvantage of the gas detectors operating with the use of catalytic combustion, namely the zero drift which is due to the physical changes in the catalyst. Other disadvantages of such detectors are, for example, their sensitivity towards catalyst poisoning by interfering gases and their relative insensitivity, and these disadvantages could not be eliminated by using the method proposed in the aforementioned German Pat. No. 1,017,384. Specifically, one disadvantage of the gas sensors which operate according to the principle of catalytic combustion could not be redressed: the temperature of the platinum filament is determined by the heat of combustion of the combustible gases to be detected and the electrical resistance of the platinum wire is dependent upon the temperature. The temperature of the platinum filament, however, is further dependent on a number of other conditions so that the obtained results can not be unequivocally interpreted.

Since the obtained electrical signals are dependent upon the temperature of the platinum filament, they are also dependent on the heat conductivity of the measuring or combustion chamber which is determined by the geometry of the measuring chamber. Already small and accidental deviations in the size and thickness of the platinum filament and in its position relative to the surrounding space and the walls thereof can result in differences of signal levels up to a factor of 10. Also, there can not be eliminated detrimental effects which are due to different flow conditions and accidental depositions close to the platinum filament which also are accompanied by a change in the thermal conductivity.

SUMMARY OF THE INVENTION

Therefore, with the foregoing in mind, it is a primary object of the present invention to provide a new and improved method of, and apparatus for, detecting at least one reducing gas in a gas mixture to be investigated, particularly in air, and which have improved sensitivity.

Another and more specific object of the present invention is directed to the provision of a new and improved method of, and apparatus for, detecting at least one reducing gas in a gas mixture to be investigated, particularly in air, and which have a considerably lower current consumption.

Still a further significant object of the present invention is directed to a new and improved method of, and apparatus for, detecting at least one reducing gas in a gas mixture to be investigated, particularly in air, which are not or only little affected by changes in the environmental conditions, like pressure, temperature or water vapor concentration.

Another, still important object of the present invention is directed to a new and improved method of, and apparatus for, detecting at least one reducing gas in a gas mixture to be investigated, particularly in air, in which the dependence upon the presence of water vapor can be compensated for in a simple manner.

Still another significant object of the present invention is directed to a new and improved method of, and apparatus for, detecting at least one reducing gas in a gas mixture to be investigated, particularly in air, which enable identification of the nature of the at least one reducing gas which is present in the gas mixture to be investigated.

Now in order to implement these and still further objects of the invention, which will become more readily apparent as the description proceeds, the method of the present development is manifested by the features that, the gas mixture to be investigated is at least partially and periodically exchanged against a reference gas having no or a smaller content of the at least one reducing gas. A selected property, such as the electrical conductivity of the gas sensor changes thereby in a periodic manner and the variation with time of such periodically varying electrical conductivity is evaluated in an evaluation circuit arrangement for detecting and/or for determining the concentration and/or for identifying the nature of the at least one reducing gas which is present in the gas mixture to be investigated.

According to a preferred embodiment of the inventive method there is used a gas detector comprising a reference chamber which is closed towards the external or environmental atmosphere and which contains a gas or air displacement means or generator and further comprising a measuring chamber which is in flow communication with the reference chamber through at least one connecting aperture or opening and which is provided with an inlet opening for admitting the gas mixture to be investigated. The gas mixture to be investigated is periodically sucked or drawn into the measuring chamber through the inlet opening thereof during a suction phase due to increasing the volume of the reference chamber by means of the gas displacement means or generator. The at least one reducing gas is at least partially removed in the measuring chamber by means of the gas sensor and a reference gas mixture which contains a lower concentration of the at least one reducing gas or which is free of the at least one reducing gas is drawn into the reference chamber through the at least one connecting aperture during such suction phase. During a venting phase, due to a decrease in the volume of the reference chamber by means of the gas displacement means or generator, this reference gas mixture is vented or passed through the measuring chamber.

The temperature variations of the gas sensor and also the gas exchange are performed simultaneously and conjointly with each other, however, not necessarily with the same duration of the related cycles or periods. Consequently, there appears a complicated but periodical variation of the electrical conductivity of the gas sensor with time. From such periodic variation with time there can be detected the presence of reducing gases in general, the presence of a specific reducing gas and also the concentration thereof.

In accordance with a preferred embodiment of the inventive method the gas mixture to be investigated is sucked through the measuring chamber into the reference chamber which is closed to the external or environmental atmosphere. The gas mixture is then vented again or blown-out through the measuring chamber. During the intake into the measuring chamber the gas mixture to be investigated passes over and/or through the gas sensor. During the venting operation the gas mixture to be investigated leaves the measuring chamber and is replaced by a gas mixture which contains none or only a small concentration of the gas to be detected. As a result, the gas sensor shows an electric conductivity which changes periodically in correspondence to the higher concentration of the reducing gas during the intake and in correspondence to the lower concentration of the reducing gas during the venting operation. Simultaneously the temperature of the gas sensor is subject to a periodic variation in a temperature or heating cycle and thereby the electrical conductivity of the gas sensor is additionally affected. In its entirety, therefore, the electrical conductivity of the gas sensor is subject to a periodic variation which is characteristically altered by the presence of reducing gases in the gas mixture to be investigated.

The temporally varying electrical conductivity of the gas sensor is converted in an evaluation circuit arrangement into a voltage signal. This voltage signal is measured either in a continuous manner or only at certain predetermined time intervals. The thus obtained measuring results are compared to reference values. There can thus be determined or decided which kinds and which concentrations of the detected reducing gases are present in the gas mixture to be investigated.

In accordance with a further preferred embodiment of the inventive method the time duration of the gas exchange period is selected such as to be substantially shorter, at least by a factor of 2, better, however, by a factor in the range of 5 to 10, than the period or cycle of temperature variations. The temperature or heating cycle of the gas sensor and the gas exchange period of the gas mixture to be investigated are matched to each other in such a manner that a plural number of gas exchange periods fall within one temperature or heating cycle. In such case the gas sensor of the gas detector used in accordance with the method of the invention shows an electric conductivity which is composed of a first component which varies slowly and at the frequency of the temperature or heating cycle and of a component which is modulated with the frequency of the gas exchange period and which changes its sign. The components of the electrical conductivity are separated in the evaluation circuit arrangement into a slowly varying d.c.-voltage signal and into an a.c.-voltage signal. At least the a.c.-voltage signal is then utilized for detecting the at least one reducing gas.

According to a specifically preferred embodiment of the inventive method the time duration of the gas exchange period is selected such that it coincides with twice the time duration of the temperature or heating cycle. It is particularly preferred that the temperature or heating cycle of the gas sensor and the exchange period of the gas mixture to be investigated are matched to each other in such a manner that the temperature of the semiconductor gas sensor is maintained during a high-temperature section of the heating cycle during a first part of the suction phase of the gas exchange period at a temperature which is higher by at least 50° C. than the temperature of the gas sensor during the subsequent low-temperature section of the heating cycle. Preferably, the temperature of the gas sensor is maintained at a temperature of about 350° C. During a low-temperature section of the heating cycle during a second part of the suction phase of the gas exchange period the temperature of the gas sensor is maintained at a lower value in the range of about 30° C. to about 300° C., preferably at about 50° C. During approximately the first half of the venting phase of the gas exchange period the temperature of the gas sensor is maintained at the same high value and during approximately the second half of the venting phase the temperature of the gas sensor is maintained at the same low value as during the suction phase.

When a pellistor which operates according to the principle of catalytic combustion is used in the inventive method, the temperature of the pellistor during the low-temperature section of the heating cycle is in the range of about 100° C. to about 650° C., preferably at about 300° C., and during the high-temperature section of the heating cycle the temperature of the pellistor is higher by at least 50° as compared to the low-temperature section of the heating cycle, preferably at about 450° C.

The increase and the decrease of the temperature of the gas sensor within a heating cycle must not occur abruptly but can also be carried out at a slow rate; the heating rate and the cooling rate need not conform with each other. Also, the start of a temperature or heating cycle need not necessarily conform with the start of a gas exchange period but the two cycles or periods can also run side-by-side and at a time offset from each other.

According to a further particularly preferred embodiment of the inventive method the required reference gas mixture which is freed of the at least one reducing gas to the largest possible degree, is prepared in a most simple manner by drawing in the gas mixture to be investigated by means of a piston. The gas mixture is passed through the gas sensor which is heated by the heating means and/or over the gas sensor and is then forced back in such a manner that practically the entire gas mixture to be investigated and located within the measuring chamber is contacted with the surface of the gas sensor. A complete conversion or the most complete possible conversion of the reducing gases at the surface of the gas sensor is thereby obtained. Consequently, and during venting of the measuring chamber due to forcing back the piston, the gas sensor is passed by a gas mixture to be investigated which is practically free of reducing gases.

As a gas sensor in carrying out the inventive method there can be used a semiconductor gas sensor which preferably contains a metal oxide semiconductor. However, there can also be used a pellistor which operates in accordance with the principle of catalytic combustion.

In a gas detector which is used in a preferred embodiment of the inventive method the volume of the members through which the gas mixture to be investigated is passed, is maintained as small as possible in order to reduce the clearance volume to a minimum.

As alluded to above, the invention is not only concerned with the aforementioned method aspects, but also relates to a novel construction of apparatus for the performance thereof. Generally speaking, the inventive apparatus comprises means for detecting at least one reducing gas in a gas mixture to be investigated, particularly in air.

To achieve the aforementioned measures, the inventive apparatus, in its more specific aspects, comprises:

a measuring chamber provided with an inlet opening for admitting the gas mixture to be investigated and provided with a gas sensor which can be heated to a predetermined temperature;

a reference chamber which is in communication with the measuring chamber through at least one aperture or opening and which comprises means for periodically drawing or sucking in the gas mixture to be investigated from the measuring chamber into the reference chamber during a suction phase and which forces back a gas mixture practically free from reducing gases into the measuring chamber during a venting phase; and the volumes of the measuring chamber and of the reference chamber are matched to each other in such a manner that during each suction phase fresh gas mixture to be investigated is drawn into the measuring chamber and during each venting phase at least a part of the gas mixture to be investigated leaves the measuring chamber through the inlet opening thereof.

There can also be provided an outlet opening which is separated from the inlet opening of the measuring chamber.

The means for sucking and venting the gas mixture to be investigated comprises a conventional gas or air displacement means or generator. Preferably this gas or air displacement means or generator forms a wall or the portion of a wall of the reference chamber and the movement or displacement thereof periodically changes the volume of the reference chamber according to a predetermined frequency.

According to a preferred embodiment of the inventive apparatus the gas or air displacement means or generator can be constructed as an electromagnetically, electrostatically, piezoelectrically or thermomechanically excitable membrane which may be constructed in the manner of a loudspeaker. The air or gas displacement means or generator may comprise a piezo foil made of, for example, polyvinylidenedifluoride. Also, the air or gas displacement means or generator may contain a dimorphic piezoelectric or bimetallic element. The air or gas displacement means or generator may also comprise a thin silicon foil which is produced by a micro-lithographic process.

In accordance with a preferred embodiment of the inventive apparatus a Philips-Woofer AD 4060/W4 is used as the air or gas displacement means or generator.

In order to achieve an improved control of the flow of the reference gas and of the flow of the gas mixture to be investigated, the gas detector in the inventive apparatus preferably may contain membrane valves which automatically pass or block the gas flow depending on the direction of flow.

According to a further preferred embodiment of the inventive apparatus the reference chamber is constructed such that it has a larger volume than the measuring chamber. There is thus insured, on the one hand, that the content of the measuring chamber is replaced by fresh gas mixture during each gas exchange period. On the other hand, due to the fact that one wall of the reference chamber forms an oscillating membrane which has a relatively large surface area, the gas which is present in the measuring chamber is exchanged to a large extent or nearly completely and at small energy consumption already at a small oscillation amplitude of the wall which forms the oscillating membrane.

According to a further preferred embodiment of the inventive apparatus a protective membrane is arranged in front of the oscillating membrane and such protective membrane protects the movable or displaceable membrane from the action of elevated temperatures.

In accordance with a further preferred embodiment of the inventive apparatus the reference chamber is constructed in such a manner that its volume becomes practically zero during the venting operation. This can be achieved, for example, by constructing the air or gas displacement means or generator in the manner of an oscillating membrane which sealingly engages an abutment, for example a conical abutment during the venting operation.

According to further embodiments of the inventive apparatus an additional gas-adsorbing filter is located in the reference chamber, preferably within the at least one connecting aperture interconnecting the measuring chamber and the reference chamber. In addition or instead of such filter a further filter of such type can be arranged in front of the inlet opening. Filters of this type can be regenerated by heating after certain predetermined time intervals.

In accordance with a further preferred embodiment of the inventive apparatus a second sensor or reference sensor can be located in the reference chamber and such second sensor responds only to, for example, water vapor.

In a further preferred embodiment of the inventive apparatus the measuring chamber and the reference chamber may directly merge with each other without a restriction therebetween. Consequently, the gas sensor is located within a chamber which constitutes the measuring chamber as well as the reference chamber. At least one wall or the part of such wall may be constructed as the air or gas displacement means or generator.

The evaluation circuit arrangement detects the electrical conductivity of the gas sensor and generates a voltage signal which is mathematically related to the electrical conductivity. The nature of this mathematical function can be either linear or non-linear, for example, logarithmic with respect to the electrical conductivity and this function is determined by the selected electronic circuits in the evaluation circuit arrangement.

The evaluation circuit arrangement may continuously measure the aforementioned voltage, derive suitable values therefrom and compare such values with stored values. The evaluation circuit arrangement also may sample the aforementioned voltage only at predetermined moment of times, for example, at the end of each period of the temperature or heating cycle and compare this voltage with other values, for example, with the maximum value appearing during the suction phase. From such comparisons the evaluation circuit arrangement which entirely or only partially is contained in the gas detector used in the inventive method, is enabled to decide whether reducing gases are present in the gas mixture to be investigated, of which nature such reducing gases are and at which concentration they are present.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings there have been generally used the same reference characters to denote the same or analogous components and wherein:

FIG. 1 is a simplified cross-sectional view through a first embodiment of the inventive apparatus;

FIG. 6 is a graph showing the variation of the difference of electrical conductivities of the gas sensor during the low-temperature heating sections of the temperature cycle as a function of the concentration of certain reducing gases in a gas detector operation as illustrated in FIGS. 4a to 4c;

FIG. 8 is a graph illustrating the relation between the electrical conductivity measured during a low-temperature section of the heating cycle during the suction phase and the concentration of reducing gas in a gas detector operation as illustrated in FIGS. 4a to 4c;

FIG. 9 illustrates a number of possible combinations of temperature or heating cycles and gas exchange periods;

FIG. 10 schematically illustrates in a number of different graphs possible shapes of the temperature cycles and of the gas exchange periods and their combinations;

FIG. 11 is a schematic cross-sectional view of a third embodiment of the inventive apparatus;

FIG. 22 is a schematic cross-sectional view of an eleventh embodiment of the inventive apparatus.

DETAILED DESCRIPTION OF THE PREFERRED EMBODIMENTS

Figure 2:
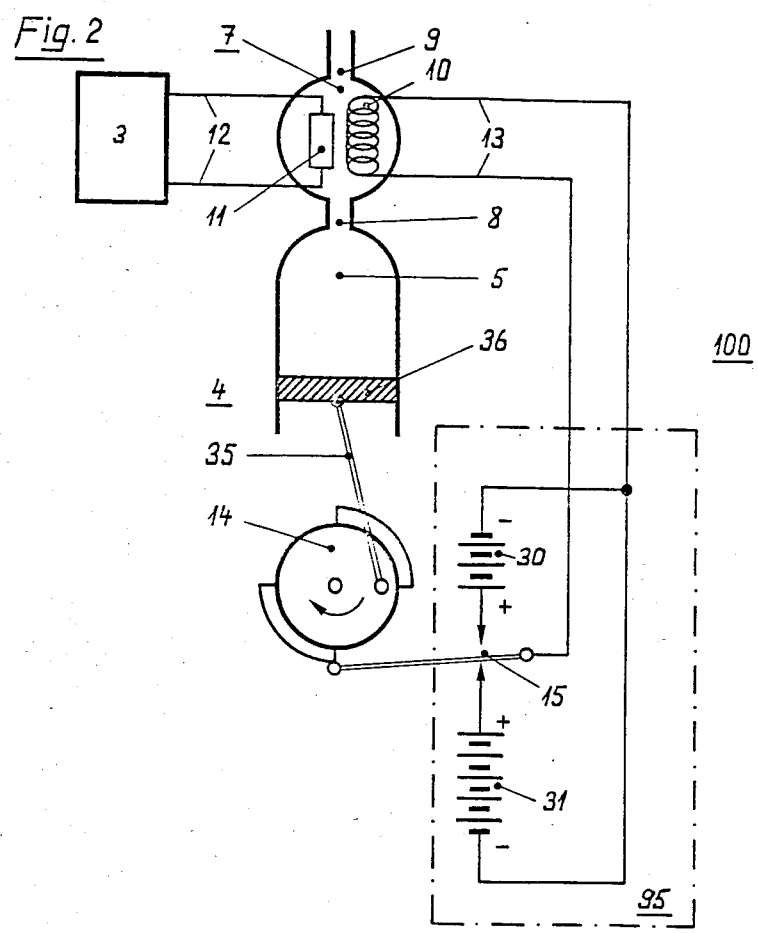
FIG. 2 is a simplified cross-sectional view of a second embodiment of the inventive apparatus.

Describing now the drawings, it is to be understood that only enough of the construction of the gas detection apparatus has been shown as needed for those skilled in the art to readily understand the underlying principles and concepts of the present development, while simplifying the showing of the drawings. Turning attention now specifically to FIG. 1, there has been schematically illustrated in a cross-sectional view a first embodiment of the inventive gas detection apparatus. A gas detector 100 thereof substantially comprises a measuring chamber 7 provided with a self-sealing membrane valve 161. A gas sensor 11 containing a metal oxide semiconductor is located within the measuring chamber 7 and is provided with heating means 10. A gas or air displacement chamber 160 comprises four self-sealing membrane valves 162, 163, 164 and 165 as well as an air or gas displacement means or generator 4 which enables the gas mixture to be investigated, which is conveniently designated by reference numeral 170 and which is present in the measuring chamber 7, to be periodically replaced by a reference gas mixture 180 and to vent or blow-off the gas mixture through the vent opening 91.

A heating voltage source 95 supplies electrical current to the heating means 10 through supply lines 13. The gas sensor 11 is thereby periodically heated to predetermined temperatures as a function of the gas exchange. The heating means 10 may surround the gas sensor 11 or may be inserted into the material of the gas sensor 11; the heating means 10 may also be located only on one side or on two or more sides of the gas sensor 11.

In the simplified manner illustrated in FIG. 1 the air or gas displacement means or generator 4 comprises a thin piezoelectric dimorphic membrane which periodically flexes towards the left or towards the right by applying an a.c.-voltage from a driver unit 55 to wires or leads 140. As a result, the volume of the left half of the air or gas displacement chamber 160 is periodically reduced and the volume of the right half of the air or gas displacement chamber 160 is periodically increased and vice versa.

The gas sensor 11 is connected to an electronic evaluation circuit arrangement 3 by means of electrical conductors 12.

After passing the gas sensor 11 the gas mixture to be investigated and designated 170 as well as the reference gas mixture designated 180 leaves the measuring chamber 7 through the vent opening 91 thereof.

In the following description the mode of operation of the gas detector 100 which is schematically illustrated in FIG. 1, will now be described with reference to FIG. 3.

The gas mixture to be investigated and designated 170 is drawn into the left half of the air or gas displacement chamber 160 by moving or displacing the air or gas displacement means or generator 4 towards the right. During this movement or displacement of the air or gas displacement means or generator 4 the membrane valve 163 is automatically opened and the membrane valve 162 is automatically closed. Simultaneously with this movement or displacement of the air or gas displacement means or generator 4 the reference gas mixture 180 which is present in the right-hand half of the air or gas displacement chamber 160 is forced into the measuring chamber 7 due to the automatic closing of the membrane valve 165 and the automatic opening of the membrane valve 164. The reference gas mixture 180 thereby displaces the gas mixture to be investigated and designated 170 which is present within the measuring chamber 7. The gas mixture to be investigated and designated 170 leaves the measuring chamber 7 via the automatically opening membrane valve 161 and through the vent opening 91. During the movement or displacement of the air or gas displacement means or generator 4 towards the right the reference gas mixture 180 surrounds and penetrates the gas sensor 11. During the subsequent movement or displacement of the air or gas displacement means or generator 4 towards the left the gas mixture to be investigated and designated 170 which is present in the left half of the air or gas displacement chamber 160 is analogously forced into the measuring chamber 7 and surrounds and penetrates the gas sensor 11.

During the aforementioned gas exchange in the measuring chamber 7 the temperature of the gas sensor 11 is alternatingly maintained at a high temperature of about 330° C. and at a low temperature of about 60° C. by the heating means 10 which are controlled by the heating voltage source 95. Preferably the duration of the gas exchange period 27 is selected such that it is substantially shorter than the duration of the temperature or heating cycle as illustrated in FIGS. 3a to 3c.

The volumes of the measuring chamber 7 and of the air or gas displacement chamber 160 as well as the amplitude of the movement or displacement of the air or gas displacement means or generator 4 are matched to each other in such a manner that the measuring chamber 7 is periodically filled by either the gas mixture to be investigated and designated 170 or by the reference gas 180 as completely as possible. The volume of the gas sensor 11 and the volume of the measuring chamber 7, on the other hand, are matched or coordinated to each other in such a manner that the gas sensor 11 fills the measuring chamber 7 as completely as possible.

Figure 3A:
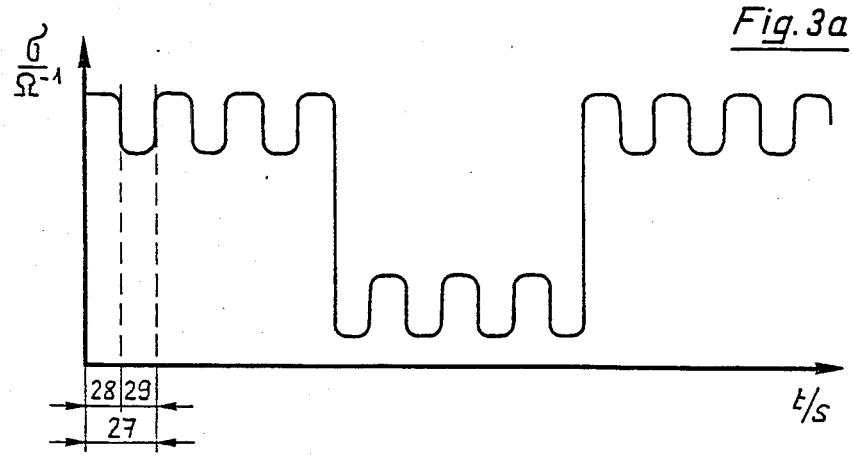
FIG. 3a is a graph showing the electrical conductivity $\sigma$ in $\Omega^{-1}$ as a function of time t in the apparatus shown in FIGS. 1 and 2 in the case that the duration of the temperature or heating cycle therein is longer than the duration of the gas exchange period.
Figure 3B:
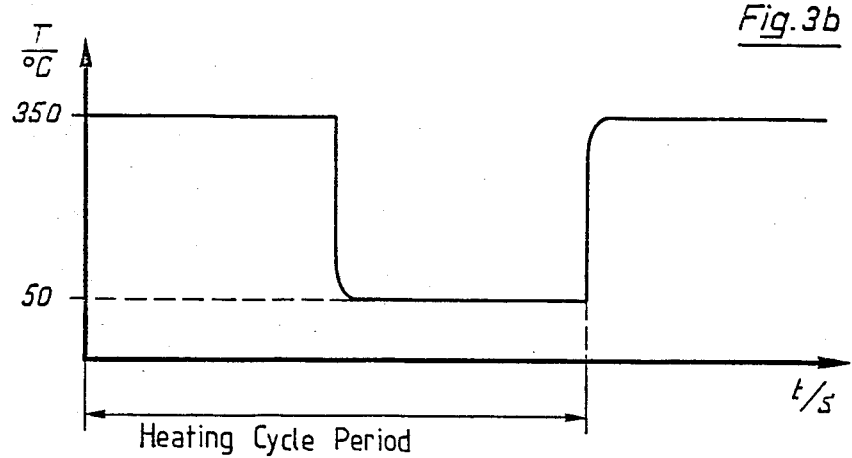
FIG. 3b is a graph showing the variation of the temperature of the gas sensor in the apparatus shown in FIGS. 1 and 2 as a function of time.
Figure 3C:
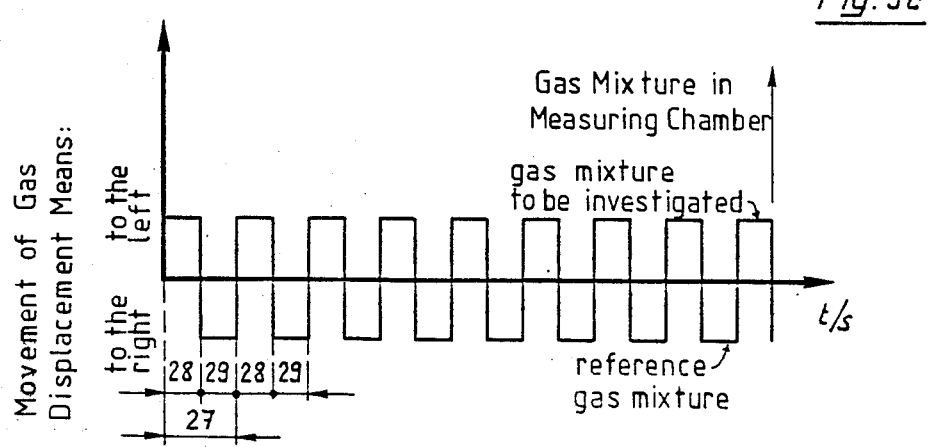
FIG. 3c is a graph illustrating the direction of displacement of the air or gas displacement means or generator 4 in the apparatus shown in FIG. 1 and the composition of the gas in the measuring chamber.

In FIG. 3a the electrical conductivity $\sigma$ of the gas sensor 11 is plotted in $\Omega^{-1}$ against the time t in seconds. In FIG. 3b the temperature of the gas sensor 11 is illustrated at the same time scale. In FIG. 3c there are shown the movement or displacement direction of the air or gas displacement means or generator 4 and the type of gas mixture present in the measuring chamber 7 as a function of time t in the first embodiment of the inventive gas detector 100 illustrated in FIG. 1.

Considering the time dependency of the electrical conductivity $\sigma$ of the gas sensor 11 it will be recognized that the electrical conductivity $\sigma$ generally and periodically varies about a high value during the time period of high heating voltage which, in the illustrated example has a value of 5.5 V which results in a gas sensor temperature of about 330° C. The duration of the period of the variations in the electrical conductivity corresponds to the duration of the gas exchange period 27. Consequently, the electrical conductivity $\sigma$ is higher when the gas mixture to be investigated and designated 170, which contains reducing gases, is present in the measuring chamber 7. The electrical conductivity $\sigma$ is lower when the reference gas mixture 180, which contains none or only a small concentration of reducing gases, is present in the measuring chamber 7. When the temperature of the gas sensor 11 is lowered to about 60° C. which is effected in the illustrated example by lowering the heating voltage to about 0.6 V, the gas sensor 11 assumes an electrical conductivity $\sigma$ which generally and periodically varies about a lower value. Again, the duration of the period of such variations conforms with the gas exchange period 27. The magnitude of the variations in the electrical conductivity $\sigma$ at the lower temperature of the gas sensor 11, however, is different from the magnitude of the variations of the electrical conductivity $\sigma$ at the higher temperature of the gas sensor 11.

Experiments have shown that the ratio of the amplitude of the variations in the electrical conductivity $\sigma$ of the gas sensor 11 at the higher heating temperature to the amplitude of such variations at the lower heating temperature depends upon the nature of the reducing gas which is contained in the gas mixture to be investigated. For example, in the case that the reducing gas is methane, the gas sensor 11 at high heating temperature shows strong variations in the electrical conductivity $\sigma$ which are synchronous with the gas exchange period 27. However, at the lower heating temperature of about 60° C., the variations in the electrical conductivity $\sigma$ are very small. In the case of hydrogen as the reducing gas, the gas sensor 11 shows great variations in the electrical conductivity $\sigma$ which are synchronous with the gas exchange period 27 at high heating temperatures as well as at low heating temperatures.

The evaluation circuit arrangement 3 converts the periodic variations of the electrical conductivity σ into an a.c.-voltage signal which has a period substantially equal to the gas exchange period 27. The amplitude of the a.c.-voltage signal is determined by the evaluation circuit arrangement 3. On the basis of the ratio of the a.c.-voltage signal amplitudes at high and at low heating temperature the evaluation circuit arrangement 3 determines the kind of reducing gas which is present in the gas mixture to be investigated and designated 170. If, for example, the a.c.-voltage signal amplitude exceeds a critical value, for example, at high temperature, and if the evaluation circuit arrangement 3 has detected the presence of a dangerous gas, the evaluation circuit arrangement 3 triggers an alarm signal.

FIGS. 4 and 5 show different time cycles for the temperature and for the gas exchange which can also be produced in the first embodiment of the inventive apparatus or gas detector 100 illustrated in FIG. 1. For this purpose the duration of the gas exchange period 27 and the duration of the temperature or heating cycles are matched to each other in an appropriate manner.

For simplification FIGS. 4 and 5 will be discussed hereinbelow with reference to the specifically preferred gas detector 100 which is illustrated in FIG. 2 showing a second embodiment of the inventive apparatus.

When the reference gas or reference gas mixture 180 is not free from reducing gases but contains a precisely known concentration of reducing gas, the inventive apparatus illustrated in FIG. 1 can also be used for continuously preparing, monitoring and regulating a gas mixture intended to contain reducing gases only in predetermined concentrations When the reference gas mixture 180 and the gas mixture to be investigated and designated 170 have the same concentration of reducing gases, the a.c.-voltage signal which is caused by the gas exchange assumes a minimum value or even becomes zero. In such case the evaluation circuit arrangement 3 is utilized as a regulation unit in order to adjust the concentration of the gas mixture to be prepared such that these a.c.-voltage signals have a minimum amplitude. When the gas mixture to be prepared is intended to contain, for example, hydrogen as well as methane in precisely determined concentrations, the a.c.-voltage signals must assume minimum values at high temperatures as well as at low temperatures which can be achieved by appropriate adjustment of the addition of hydrogen or methane to the gas mixture to be prepared and which can be monitored by the evaluation circuit arrangement 3 in combination with the gas detector 100 in the inventive apparatus.

FIG. 2 shows a schematic and cross-sectional illustration of a second embodiment of the inventive gas detector 100. This embodiment substantially comprises a measuring chamber 7 in which there is located the gas sensor 11 which is provided with heating means 10. The gas detector 100 further comprises a reference chamber 5 in which there is located an air or gas displacement means or generator 4, i.e. a device or means enabling the gas mixture which is present in the measuring chamber 7 to be replaced by a gas mixture which is present in the reference chamber 5. Furthermore, there is provided a heating voltage source 95 by means of which the gas sensor 11 is periodically heated to predetermined temperatures as a function of the gas exchange in the measuring chamber 7. The heating means 10 may surround the gas sensor 11 or may be inserted into the material of the gas sensor 11. The heating means 10 may also be located on only one side or on two or more sides of the gas sensor 11.

In the illustrated simplified embodiment the air or gas displacement means or generator 4 comprises a plate or eccentric disk 14 which is driven by a not particularly illustrated drive motor. The plate or eccentric disk 14 periodically reciprocates a piston 36 by means of a connecting rod 35 and the volume of the reference chamber 5 is thereby periodically varied. Cams are provided at the plate or eccentric disk 14 and operate upon a microswitch 15 in such a manner that different heating voltages are alternatingly supplied to the heating means 10 from two power sources 30 and 31 via lines or conductors 13.

The gas sensor 11 is connected to the evaluation circuit arrangement 3 by electric lines or conductors 12. The gas mixture to be investigated is supplied to the measuring chamber 7 through the inlet opening 9. The measuring chamber 7 is connected to the reference chamber 5 by means of the at least one connecting aperture or opening 8.

In the following description the mode of operation of the second embodiment of the inventive gas detector 100 schematically illustrated in FIG. 2 will now be described with reference to FIGS. 4 and 5 and will be compared in this description with the mode of operation of a hitherto usual gas sensor.

The gas mixture to be investigated is periodically drawn in through the measuring chamber 7 into the reference chamber 5 by means of the air or gas displacement means or generator 4 during a suction phase 28 of the gas exchange period 27. The gas is then periodically vented or forced out again through the measuring chamber 7 by means of the air or gas displacement means or generator 4 during a venting phase 29 of the gas exchange period 27. During this gas exchange period 27 the temperature of the gas sensor 11 is alternatingly maintained at a high temperature of about 350° C. during a high-temperature section and at a low temperature of about 50° C. during a low-temperature section of the heating cycle by the heating means 10. In a preferred embodiment of the inventive method which is carried out by the inventive gas detector illustrated in FIG. 2, the duration of the gas exchange period 27 is selected such that it conforms with twice the duration of the temperature or heating cycle as illustrated in FIGS. 4 and 5.

Figure 4A:
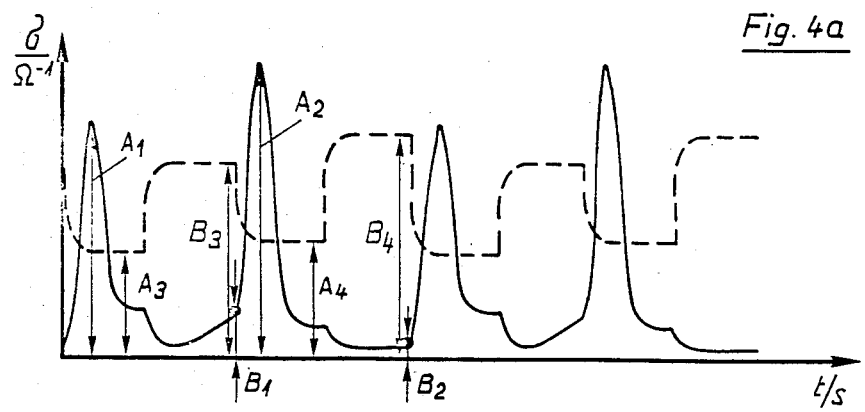
FIG. 4a is a graph showing the electrical conductivity $\sigma$ in $\Omega^{-1}$ as a function of time t in the apparatus shown in FIGS. 1 and 2 in the case that the duration of the temperature or heating cycle is half the duration of the gas exchange period.
Figure 4B:
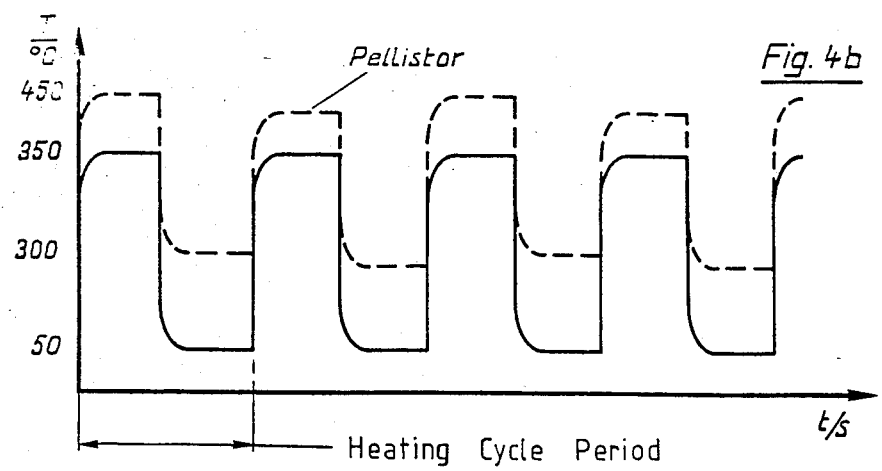
FIG. 4b is a graph showing the variation of the temperature of the gas sensor as a function of time.
Figure 4C:
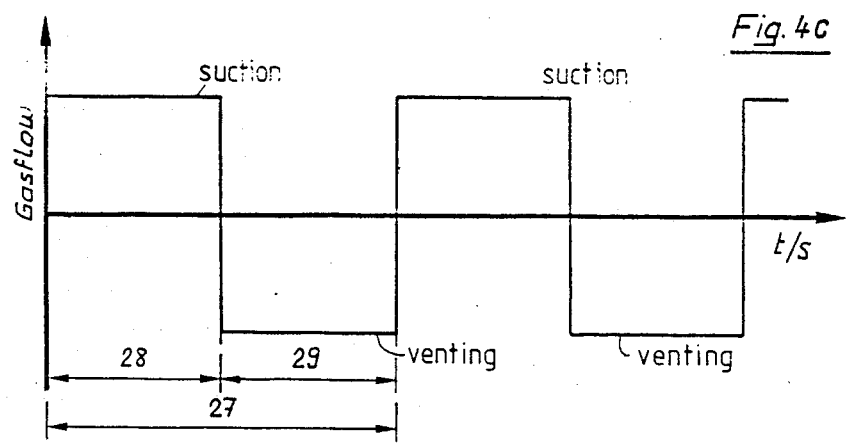
FIG. 4c is a graph showing the flow direction through the measuring chamber at the inlet opening thereof in the apparatus shown in FIGS. 1 and 2.
Figure 5A:
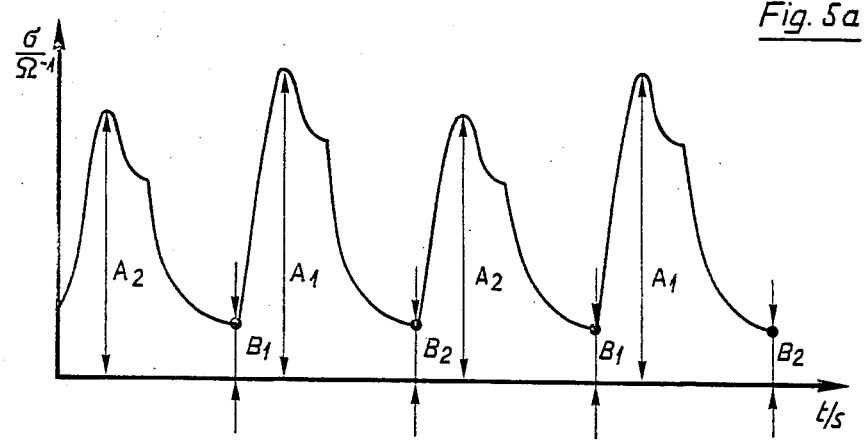
FIG. 5a is a graph showing the electrical conductivity $\sigma$ in $\Omega^{-1}$ as a function of time t as shown in FIG. 4a, however, with a different heating cycle but at the same ratio of the durations of the heating or temperature cycle in relation to the duration of the gas exchange period.
Figure 5B:
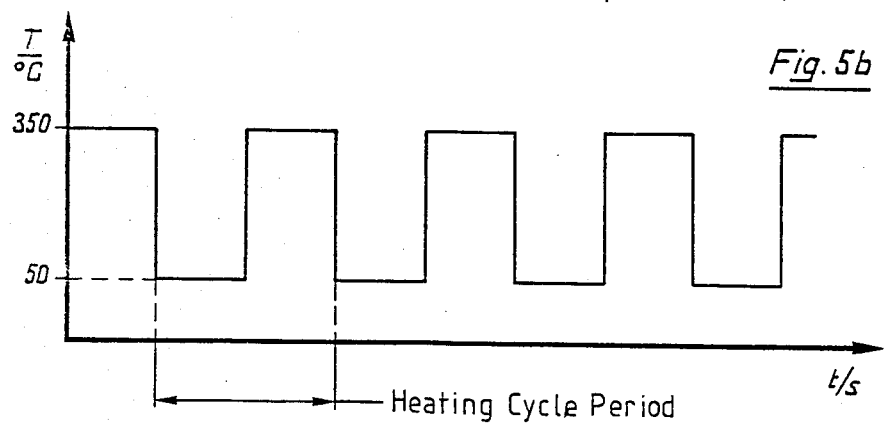
FIG. 5b is a graph showing the variation of the temperature of the gas sensor as a function of time.
Figure 5C:
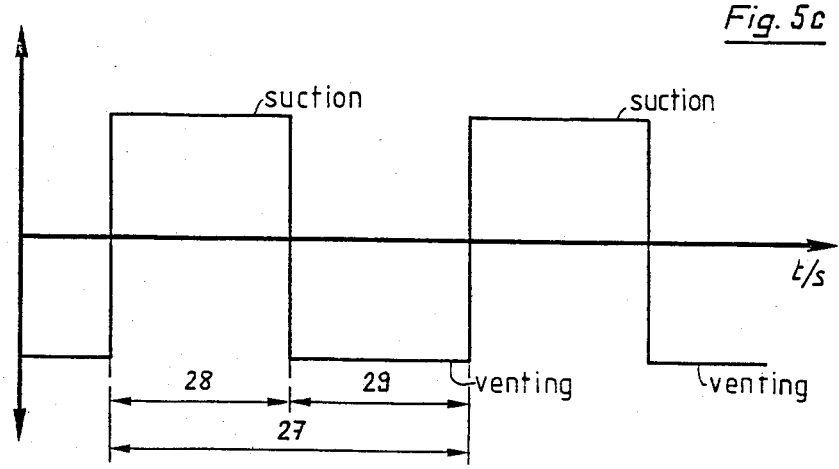
FIG. 5c is a graph showing the flow direction through the measuring chamber at the inlet opening thereof.

In FIGS. 4a and 5a there is plotted on the ordinate the electrical conductivity σ in $\Omega^{-1}$ against the time t in seconds on the abscissa. In FIGS. 4b and 5b there is indicated the temperature of the gas sensor 11 at the same time scale. In FIGS. 4c and 5c there is shown the gas flow in the measuring chamber 7 at an inlet opening 9 thereof.

The continuous line drawn in FIG. 4a relates to the electrical conductivity σ of the semiconductor gas sensor 11 and the broken line relates to the temperature of a pellistor gas sensor 11. In the following there will only be described the behavior of a semiconductor gas sensor 11. The behavior of a pellistor gas sensor 11 will only be described with reference to FIG. 15.

Considering the electrical conductivity σ of the gas sensor 11 as a function of time, it will be recognized that during the suction phase 28 and at high heating voltage, in the illustrated embodiment 6 V, which correspond to a temperature of the gas sensor 11 of 350° C., there is obtained a first peak, the so-called oxidation peak $A_1$. Thereafter the signal decreases again and reaches a minimum after the heating voltage is switched to 0.5 V which corresponds to a temperature of the gas sensor 11 of about 50° C. The signal rises then again and reaches a point $B_1$ which is the so-called adsorption peak. At this moment of time the temperature of the gas sensor 11 is again increased to about 350° C. and there now begins the venting phase 29 of the gas exchange period 27. During this period a reference gas flows through the measuring chamber 7 and this reference gas is practically free of the gas to be detected or contains only a smaller concentration thereof. There is thus obtained a second oxidation peak $A_2$. Thereafter the output signal decreases again and reaches a minimum again after lowering the temperature of the gas sensor 11 to about 50° C. During the venting phase 29 of the gas exchange period 27 the signal does not again reach the level of the adsorption peak $B_1$ but remains at a much smaller value $B_2$. At this moment of time there is again switched the temperature of the gas sensor 11 to about 350° C. and there begins a further suction phase 28. There is again obtained a first oxidation peak $A_1$ and there is again obtained an adsorption peak $B_1$ after the temperature of the gas sensor 11 is changed to 50° C. For the detection of reducing gases there is formed the difference $\Delta\sigma$ from the adsorption peaks $B_1$ and $B_2$, i.e.

$$\Delta\sigma = B_1 - B_2.$$

During the suction phase 28 air or gas plus the gas to be detected and also in addition humidity reach the gas sensor 11. There thus result the first oxidation peak $A_1$ and the first adsorption peak $B_1$. Since the gas mixture contains reducing gases, the reducing gases can be adsorbed at the gas sensor 11 and correspondingly the output signal of the gas sensor 11 increases up to the value of $B_1$. The gas sensor 11 is now fully loaded with reducing gases which are oxidized in the next-following heating period during the venting phase 29 and result in the high oxidation peak $A_2$. During the further part of the venting phase 29 the gas sensor 11 is cooled. Since now only the reference gas plus humidity flows over the gas sensor 11, no reducing gases can be adsorbed at the gas sensor 11. Consequently, there is not present any adsorption peak and the adsorption peak $B_2$ is correspondingly small. During the next-following suction phase 28 there begins a further gas exchange period 27 which comprises the heating cycle of the gas sensor 11 and the gas exchange period 27 of the gas mixture. In the evaluation circuit arrangement 3 there is now formed the difference $\Delta\sigma$ of the measured conductivities $$\Delta\sigma = B_1 - B_2.$$

This difference is a measure of the concentration of the gas to be detected.

In FIG. 5a there is indicated a further modification of the inventive method which is carried out by using the second embodiment of the gas detector 100 illustrated in FIG. 2. The gas exchange period 27 is the same as indicated hereinbefore. However, the heating cycle is modified in such a manner that, during the suction phase 28, the temperature of the gas sensor 11 is first maintained at the lower temperature of about 50° C. and then, during the second half of the suction phase 28, is maintained at the high temperature of about 350° C. There will thus be obtained the result that the difference of the adsorption peaks $B_1 - B_2$ is approximately equal to zero. The difference between the oxidation peaks $A_1$ and $A_2$, however is so great that it is suited for the detection and for the determination of the concentration of reducing gases or gases which are adsorbed at the gas sensor 11. Furthermore, from a comparison between $(A_1 - A_2)$ and $B_1$ or $(A_1 - A_2)$ and $B_2$, as well as from a comparison between $A_1$ and $B_1$ or $A_1$ and $B_2$ at a given $(A_1 - A_2)$ or $A_1$ a conclusion can be reached concerning the nature of the reducing gas.

FIG. 6 shows the values of the difference $B_1 - B_2$ which is converted by the evaluation circuit arrangement 3 into a voltage signal, as a function of the concentration of the gases carbon monoxide and methane. In this experiment the inventive gas detector 100 is operated with a temperature or heating cycle and with a gas exchange period in accordance with FIG. 4. The gas detector 100 contains a Taguchi TGS-12 semiconductor gas sensor as the gas sensor 11.

The double logarithmic illustration of FIG. 6 shows that the difference $\Delta\sigma$ of the signals $B_1 - B_2$ is dependent on the fifth power of the square root of the gas concentration, i.e.

$$\Delta\sigma = \alpha \cdot (Gas)^{5/2} \qquad \text{Equation (1)}$$

wherein $\alpha$ is a proportionality constant. An extremely sensitive detection of reducing gases or gases which are adsorbed at the gas sensor 11 is thereby provided.

The curve designated $N_{CO}$ in FIG. 6 shows in double logarithmic illustration the electrical conductivity $\sigma$ of a normal gas sensor in the presence of carbon monoxide. The electrical conductivity $\sigma$ is evaluated in the form of an electrical voltage U. There is distinctly recognizable the flatter characteristic of this curve which corresponds to an exponent $\frac{1}{2}$ in the analogous Equation (2).

$$\sigma = \alpha \cdot (Gas)^{\frac{1}{2}} \qquad \text{Equation (2)}$$

The exponent 5/2 in Equation (1) is independent of the nature of the gas, however, is observed only at higher concentrations in the case of more difficultly oxidizable gases like, for example, methane. The exponent 5/2 of a concentration dependent magnitude is totally novel in gas sensors and represents an enormous progress for constructing highly sensitive and precise gas detectors.

For relative humidities in the range of 5% to 93% at 20° C. the water vapor dependency is practically constant over the entire concentration range, so that the water vapor dependence simply can be corrected by computation if the water vapor concentration is known. The dependency is somewhat greater in the case of carbon monoxide than in the case of hydrogen, however, the dependency is also constant over the entire concentration range.

Similar curves as illustrated in FIGS. 4a and 5a result for carbon monoxide, methane, and hydrogen. The magnitude of the oxidation peaks $A_1$ and $A_2$ and their difference $A_2 - A_1$, however, are different at a given magnitude of $B_1 - B_2$ for each one of the gases hydrogen, carbon monoxide and methane. From this different behavior conclusions can be reached concerning the nature of the gas, namely hydrogen, carbon monoxide or methane.

Figure 7:
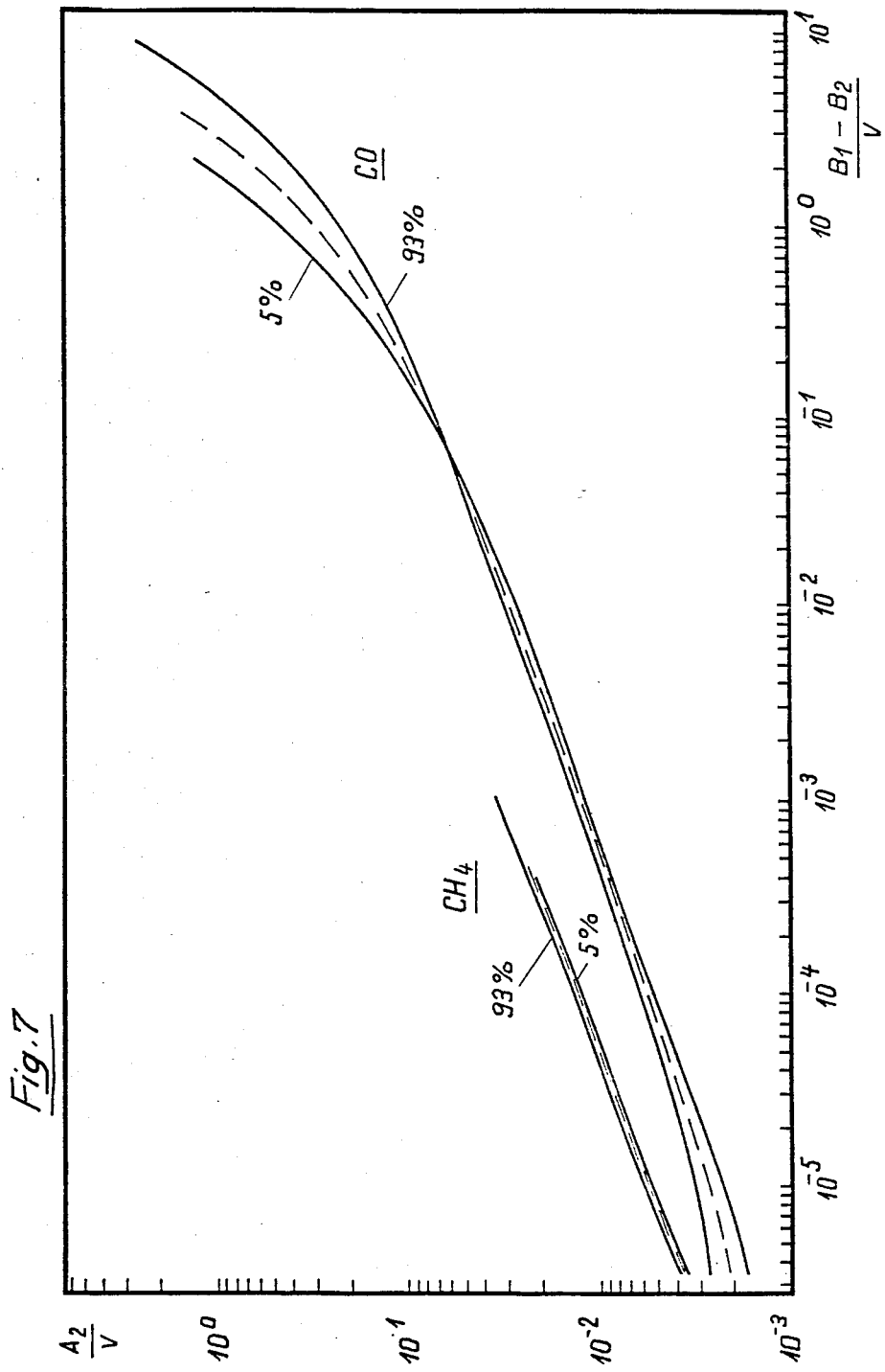
FIG. 7 is a graph showing the relation between the conductivity differences illustrated in FIG. 6 and the amplitude of the electrical conductivity during a high-temperature section of the heating cycle during the venting phase of the operation of the gas detector as illustrated in FIG. 4.

FIG. 7 shows the relation between the differences $B_1 - B_2$ and the amplitude $A_2$ for the gases methane and carbon monoxide at relative humidities in the range of 5% to 95% at 27° C. It is distinctly shown in FIG. 7 that at equally great differences $B_1-B_2$ the value of $A_2$ for carbon monoxide is significantly smaller than for methane at all investigated relative humidities. From a comparison between $(B_1-B_2)$ and $A_2$ at a given $(B_1-B_2)$ there can thus be determined the nature of the reducing gas. Such unequivocal differentiation with respect to the nature of the reducing gas which generates the change in the electrical conductivity $\sigma$ at the gas sensor 11, can be made using a single gas sensor and by means of mere computation. Such unequivocal differentiation has not been known hitherto and represents great progress with respect to selectively detecting specific gases with simultaneously extremely high sensitivity of the gas detector 100. Analogous curves to FIG. 7 result when the difference $A_2-A_1$ or solely $A_1$ is plotted against $B_1-B_2$ or against solely $B_1$, and such curves can also be evaluated with respect to identifying the nature of the reducing gases.

Instead of the difference $B_1-B_2$ measured by means of the second embodiment of the inventive gas detector 100 in carrying out the inventive method in a mode of operation as illustrated in FIG. 4, the value of $B_1$ is illustrated in FIG. 8 as a function of the concentration of the reducing gas in a double-logarithmic scale. Also in this case there will be again recognized the extremely steep rise of the measuring values with increasing concentration of the reducing gas and this rise corresponds to an exponent of approximately 4/2 in Equation (1). This also demonstrates a much higher sensitivity of the inventive method in comparison to the conventional operation of a gas sensor 11.

The time durations for the heating cycle and for the gas exchange period need not conform to one another and also the heating cycle and the gas exchange period need not start at the same moment of time, i.e. there may exist a phase shift between the heating cycle and the gas exchange period. Furthermore, these cycles need not have the same duration. For an optimal adaptation to predetermined gases the high-temperature section can be selected shorter or longer than the low-temperature section of the heating cycle. Furthermore, by varying the heating temperature and/or the cooling temperature, the selectivity can be affected with respect to certain gases. FIG. 9 shows possible forms of such cycles and also possible combinations of heating cycles and gas exchange periods.

It is furthermore not required that the heating cycles and gas exchange periods, as illustrated hereinbefore, have rectangular or symmetric shapes. By varying the rate of flow during the suction phase 28 and during the venting phase 29, as well as by varying the heating or cooling rates there can be obtained differently shaped curves for the gas exchange periods and for the heating cycles which also may be non-symmetric. Possible shapes of such kind are illustrated in FIG. 10. All such indicated curve shapes can be selected for the heating cycles and for the gas exchange periods independently of each other and can be combined with each other in any desired manner.

A third embodiment of the inventive apparatus or gas detector or arrangement for gas detection is illustrated in FIG. 11 and is specifically suited for detecting reducing gases. Such apparatus comprises a detector insert 1 which can be inserted into a socket 2 which, for example, may constitute a conventional gas detector socket. The detector insert 1 contains an electric or electronic control and evaluation circuit arrangement 3 or at least a part thereof. The remaining portion of the circuit arrangement may be arranged at a suitable central signal station which is not particularly illustrated and which is connected by suitable lines or conductors with the socket 2. The evaluation circuit arrangement 3 controls an air or gas displacement means or generator 4 which may form a wall of the following reference chamber 5 or a portion thereof. The volume of the reference chamber 5 can be periodically varied at a predetermined frequency which preferably is in the range of about 0.005 and 10 Hz and, for example, may be 0.1 Hz.

The air or gas displacement means or generator 4 may be constructed as a membrane in the manner of a loudspeaker and the membrane can be, for example, electromagnetically, electrostatically, piezoelectrically or thermomechanically excited. The air or gas displacement means or generator 4 may also comprise a piezo foil of the polyvinylidenedifluoride type or may contain a dimorphic, piezoelectric or bimetallic element. In miniaturized gas detectors which operate according to the inventive method the air or gas displacement means or generator 4 may also constitute a silicon membrane which is produced by means of a micro-lithographic process. In a practically constructed example a Philips-Woofer AD 4060/W4 has proven to be suitable as the air or gas displacement means or generator 4. However, also other types of loudspeakers can be used and there are mentioned here as possible examples the Philips loudspeakers ADO-198, ADO-1985, ADO-09, ADO-1980, AD-4472 and others. A piezo-ceramic type membrane is the Philips PXE-52 membrane The reference chamber 5 is completely closed towards the external or environmental atmosphere with the exception of the connecting aperture 8 to the measuring chamber 7. The reference chamber 5 serves as a reservoir for a reference gas or gas mixture which is at least partially freed of reducing gases and preferably is completely freed of such gases.

The reference chamber 5 is connected with the measuring chamber 7 through a connecting aperture or opening 8 of small cross-sectional area, for example 0.03 $cm^2$. A gas sensor 11 is located within the measuring chamber 7 and in the presently illustrated embodiment the gas sensor 11 constitutes a standard gas sensor TGS-812 (Taguchi/Figaro). The gas sensor 11 can be heated to a temperature in the range of 30° C. to 650° C. by heating means 10 which are supplied with electrical power through electrical lines or conductors 13. An upper temperature of 350° C. and a lower temperature of about 60° C. have proven to be the best operating temperatures. The gas sensor 11 is connected to the evaluation circuit arrangement 3 by means of electrical lines or conductors 12.

The measuring chamber 7 possesses a volume of about 0.10 $cm^3$ and the reference chamber 5 possesses a volume of about 100 $cm^3$, so that the volume ratio is greater than 1 to 1000. The ratio of the sum of the volumes of the reference chamber 5 and of the measuring chamber 7 to the sum of the volumes of the gas sensor 11 and the heating means 10 in the presently illustrated embodiment has a value of $2 \times 10^4:1$.

In an arrangement for gas detection which is analogous to the embodiment of the inventive apparatus illustrated in FIG. 11 the commercially available metal oxide gas sensor TGS-812 which possesses a volume of about 5 $mm^3$ for the sensor and the heating means has been replaced by a miniature gas sensor possessing a volume of only 0.05 $mm^3$ for the sensor and the heating means. Although the ratio of the sum of the volumes of the reference chamber 5 and of the measuring chamber 7 to the sum of the volumes of the gas sensor 11 and of the heating means 10 in this particular case even has a value of $2\times 10^7:1$, such arrangement also operated extremely satisfactorily.

During one oscillation of the air or gas displacement means or generator 4 a volume of the gas mixture to be investigated and which corresponds to the oscillation amplitude is drawn through the inlet opening 9 and through the measuring chamber 7 past the gas sensor 11 into the reference chamber 5. During this suction phase 28, see FIGS. 4a to 4c and FIGS. 5a to 5c, the gas mixture to be investigated is at least partially freed from reducing gases. In the reverse direction one oscillation of the air or gas displacement means or generator 4 forces the gas mixture or reference gas which is at least partially free from reducing gases through the connecting aperture 8 into the measuring chamber 7 and this reference gas leaves the measuring chamber 7 through the inlet opening 9 thereof, which gas flow appears during the venting phase 29 of the gas exchange period 27.

A filter 6 for adsorbing residual amounts of reducing gases or other interfering gases can be arranged in the reference chamber 5 in front of the connecting aperture 8. The filter 6 is regenerated by heating the same after predetermined time intervals. A further filter which is not particularly illustrated in FIG. 11 and which also adsorbs interfering gases, can also be arranged in front of the inlet opening 9.

A housing 16 can be slipped upon the detector insert 1 and such housing 16 comprises openings 17 for the entry of the gas to be investigated, in the presently illustrated embodiment the gas to be investigated constitutes the external or environmental atmosphere of the gas detector 100. Due to its geometric design and due to the arrangement of the openings 17 the housing 16 can be adapted to different environmental conditions.

The inlet opening 9 of the measuring chamber 7 can also be directly charged with the gas mixture to be investigated by means of a not particularly illustrated supply tube. Since the inventive method is independent of wind or air flow to a high degree, the housing 16 is not absolutely required.

In order to further increase the independence of wind or air flows or currents the inlet opening 9 can also be constructed in a further and not particularly illustrated embodiment as a capillary tube having a length of about 1 cm and an internal diameter of about 0.3 mm. The gas flow at the sensor is thus only determined by the movement or displacement of the air or gas displacement means or generator 4, and the measurements of the gas concentration thus become totally independent of the flow rate of the air or gas mixture to be investigated.

During operation of the arrangement described hereinbefore the air or gas is reciprocated between the reference chamber 5 and the measuring chamber 7 and thus also between the measuring chamber 7 and the external or environmental atmosphere at a predetermined frequency of, for example, 0.1 Hz. During this operation the entire moved or displaced air or gas volume advantageously corresponds at least approximately to the volume of the measuring chamber 7. Consequently, the volume of the measuring chamber 7 is at least partially and in the ideal case practically completely and periodically exchanged. Thus, there is alternatingly present external or environmental air, i.e. the gas mixture to be investigated, or air from the reference chamber, i.e. a gas mixture or reference gas without reducing gases in the measuring chamber 7, and thus in the region of the gas sensor 11. The moved or displaced volume is dependent upon the special geometric design of the reference chamber 5, of the measuring chamber 7, of the connecting aperture 8, of the filter 6 and of the amplitude of movement or displacement of the air or gas displacement means or generator 4.

Simultaneously the temperature of the gas sensor 11 is switched back and forth between a high value of preferably about 350° C. and a low value of preferably 60° C. Preferably, the duration of the temperature cycle is half as long as the duration of the gas exchange period and the two cycles preferably run in the time sequence illustrated in FIGS. 4a to 4c. The shape of the heating and cooling curve of the gas sensor 11 as well as of the gas exchange in the measuring chamber 7 need not absolutely correspond to the curve shown in FIGS. 4a to 4c, but also can occur according to the curves described with reference to FIG. 10.

As long as the external or environmental air or the gas mixture to be investigated does not contain any reducing gases, the difference $B_1-B_2$ of the electrical conductivity $\sigma$ of the gas sensor 11 is practically equal to zero. The evaluation circuit arrangement 3 samples the electrical conductivity $\sigma$ of the gas sensor 11 at the moments of time corresponding to $B_1$ and $B_2$, stores such values and supplies a voltage signal which is linearly related to the difference $B_1-B_2$ and is very small in the presently described case. However, as soon as the external or environmental air, i.e. the gas mixture to be investigated, contains reducing gases, the air or gas present in the measuring chamber 7 periodically changes between the air or gas having a small content of reducing gases supplied from the reference chamber 5 and air or gas from the external or environmental atmosphere, i.e. the gas mixture to be investigated, which contains reducing gases. As illustrated in FIGS. 4a to 4c, the difference $B_1-B_2$ then assumes a very large value and the evaluation circuit arrangement 3 generates, in correspondence to such large difference $B_1-B_2$, a correspondingly great voltage signal. Since the inventive method is distinguished by an extremely wide dynamic range, the value of the difference $B_1-B_2$ is preferably converted into a voltage signal in accordance with a logarithmic relation. There can also be provided means in the evaluation circuit arrangement 3 which trigger an alarm signal when a predetermined value of the voltage signal is exceeded.

The evaluation circuit arrangement 3 may contain a quotient circuit in order to form the ratio between the difference $B_1-B_2$ and either the difference $A_2-A_1$ or solely $A_2$. Such ratio, at a predetermined value of the difference $B_1-B_2$ and at constant time duration of the temperature or heating cycle and of the gas exchange period, is dependent upon the nature of the reducing gas and the evaluation circuit arrangement 3 can be designed such that, dependent on the value $B_1-B_2$, an alarm signal is only delivered when the ratio of the aforementioned values at the predetermined value of the difference $B_1-B_2$ assumes a predetermined value at which a preselected gas is present in a dangerous concentration in the gas mixture to be investigated.

The inventive method can not only be carried out using gas sensors a selected property of which changes, such as the aforementioned gas sensors 11 which change their electrical conductivity but also gas sensors which change their electrical resistance under the action of reducing gases, and furthermore, the inventive method can also be carried out using so-called optical gas sensors. Such optical gas sensors change as their selected property their optical properties under the action of certain gases. In such cases the adsorption peaks $B_1$ and $B_2$ and the oxidation peaks $A_1$ and $A_2$ correspond to different optical extinctions of the gas sensor.

Very good results can also be obtained when there is used a pellistor which operates according to the principle of catalytic combustion, instead of a metal oxide semiconductor. The inventive method is furthermore not restricted to removing the gas to be detected by oxidation or reduction, i.e. by chemical reaction, from the gas mixture to be investigated. For example, the gas to be detected can also be removed by adsorption at a solid body like, for example, the oscillator according to U.S. Pat. No. 4,399,686, granted Aug. 23, 1983, and further can also be removed by a suitable solid electrolyte or by pumping using an ion pump, for example, in the case of oxygen.

When the gas exchange period of the gas mixture to be investigated is shortened, for example from about 20 seconds in the measurements illustrated in FIGS. 4a to 4c to about 5 seconds, the exponent in the aforementioned Equation (1) assumes smaller values than 5/2. Thus the sensitivity of the gas detector 100 can be varied in a simple manner by varying the gas exchange frequency. There is thus made possible a multi-stage operation in which, for example, the gas detector 100 is operated at the most sensitive stage during night-time and a less sensitive stage is adjusted during daytime.

Figure 12:
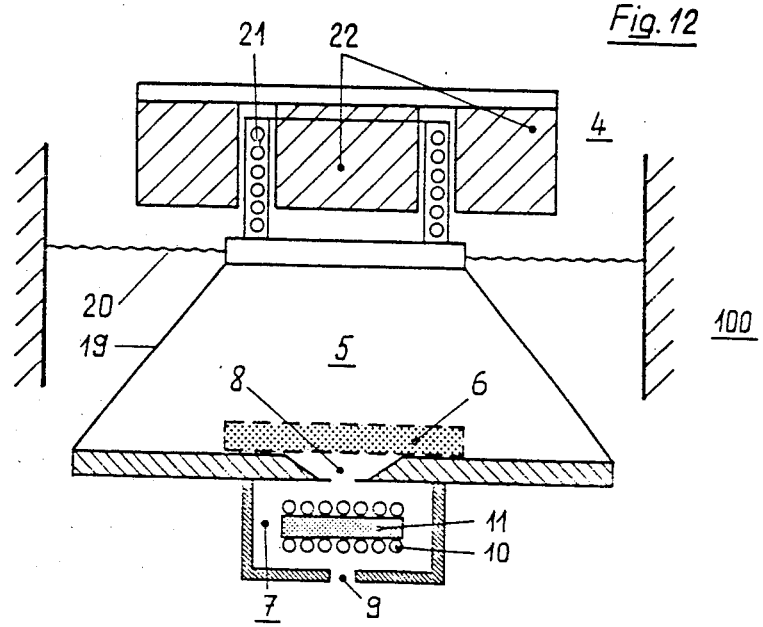
FIG. 12 is a schematic cross-sectional view of a fourth embodiment of the inventive apparatus.

A fourth embodiment of the inventive gas detector is schematically illustrated in a cross-sectional view in FIG. 12. A conically-shaped wall 19 of the reference chamber 5 is mounted at a coil 21 which is supported by resilient holding means 20. The coil 21 extends into an angular gap of a permanent magnet 22. When the coil 21 is excited by means of an alternating voltage, the conical wall 19 is made to oscillate like an electrodynamic loudspeaker, whereby the volume of the reference chamber 5 is periodically varied. During this oscillation the air or gas is periodically forced from the reference chamber 5 through the filter 6 and through the connecting aperture 8 into the measuring chamber 7 and is drawn back again.

Figure 13:
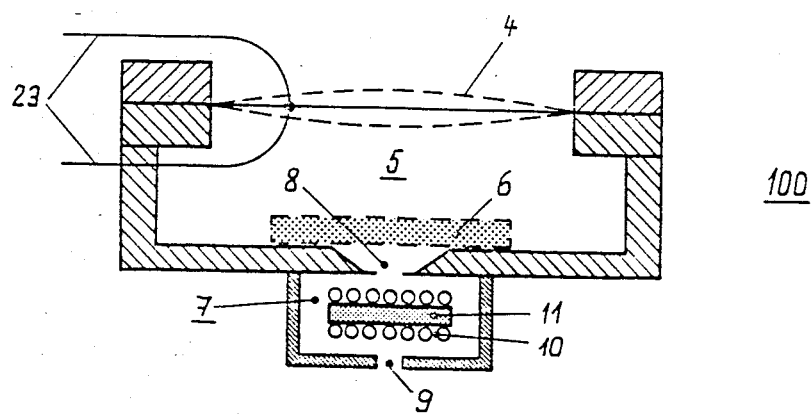
FIG. 13 is a schematic cross-sectional view of a fifth embodiment of the inventive apparatus.

A further or fifth embodiment of the inventive gas detector 100 is illustrated in FIG. 13. Therein the air or gas displacement means or generator 4 constitutes a dimorphic piezo foil. Depending on the voltage applied to the two sides thereof by means of lines or conductors 23, the piezo foil experiences a corresponding excursion. When now an alternating voltage is applied to the lines or conductors 23, the piezo foil is excited to an oscillation, the frequency of which corresponds to the applied alternating voltage. The volume of the reference chamber 5 varies or fluctuates at the same frequency.

Figure 14:
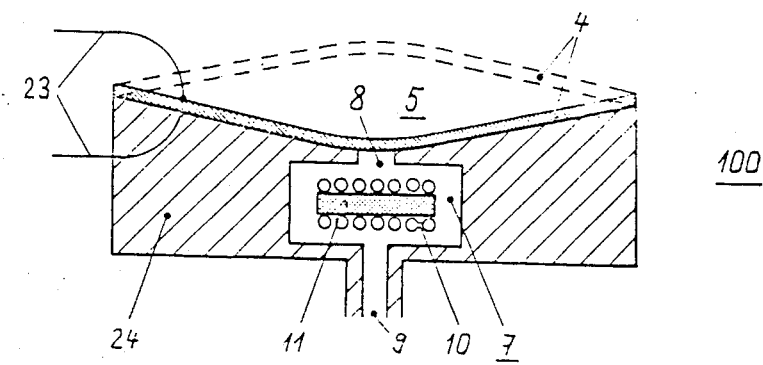
FIG. 14 is a schematic cross-sectional view of a sixth embodiment of the inventive apparatus.

A sixth embodiment of the inventive gas detector which constitutes a further development of the embodiment described hereinbefore with reference to FIG. 13, is illustrated in FIG. 14. In such further development the volume of the reference chamber 5 possesses the value zero in the final stage of the venting phase 29, that is the clearance volume practically disappears. This is achieved by a conically shaped or planar abutment 24 which is provided in the reference chamber 5 and to which the piezo foil is sealing engaged at the end of the venting phase 29. This is shown in FIG. 14 by continuous lines. At the end of the suction phase 28 the piezo foil assumes the position indicated by broken lines.

Figure 15:
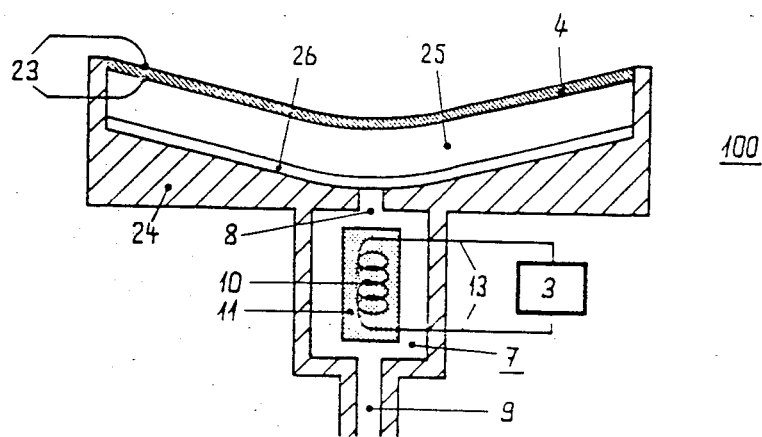
FIG. 15 is a schematic cross-sectional view of a seventh embodiment of the inventive apparatus.

A seventh embodiment of the inventive gas detector 100 is shown in FIG. 15 and constitutes a further development of the gas detector illustrated in FIG. 14. A temperature-sensitive piezo foil constitutes the air or gas displacement means or generator 4 and transmits its movement or displacement through a working volume 25 to a protective membrane 26 which, in the presently described embodiment, constitutes a temperature-resistant and very thin metal membrane having a thickness in the range of 1 to 10 $\mu$m.

In contrast to FIG. 14 where the illustrated gas sensor constitutes a semiconductor sensor, a known pellistor is used as the gas sensor 11 in the embodiment illustrated in FIG. 15. The heating means for the pellistor are formed by a heater winding 10 which forms a spiral wire and the electrical resistance of which has a strongly positive temperature coefficient. The supply lines or conductors 13 to the heater winding 10 in this case are identical with the measuring lines 12 and terminate in the evaluation circuit arrangement 3 at a not particularly illustrated heating voltage source. The heating voltage source supplies electrical power to the gas sensor 11 via the supply lines or conductors 13 and periodically heats the gas sensor 11 to about 450° C. and to about 300° C. by means of the heater winding 10.

The curve shown in broken lines in FIG. 4a shows the conductivity of the heater winding 10 as a function of time. During the suction phase 28 all reducing gases which are contained in the gas mixture to be investigated burn up at the gas sensor 11 at the high temperature of 450° C. The heat of combustion which is released during this oxidation additionally heats the heater winding 10 and thereby the electrical conductivity $\sigma$ thereof is decreased. During this suction phase 28 the gas mixture to be investigated is at least partially freed from reducing gases.

The temperature of the gas sensor 11 is then lowered to about 300° C. during the suction phase and the electrical conductivity $\sigma$ of the gas sensor drastically increases. At this lower temperature only readily oxidizable gases like, for example hydrogen, are burned up, whereas difficultly oxidizable gases like, for example, methane are not burned. The combustion heat which is released during this oxidation is therefore smaller than the heat of combustion which previously was released at the temperature of about 450° C., when the gas mixture to be investigated contains readily oxidizable reducing gases as well as difficultly oxidizable reducing gases. However, the heat of combustion released during this oxidation is substantially the same when only readily oxidizable reducing gases are present. The heat of combustion released during this oxidation is practically zero when only difficultly oxidizable reducing gases are present in the gas mixture to be investigated. This heat of combustion heats the gas sensor 11 to some degree and thereby again decreases its electrical conductivity $\sigma$ to some extent.

In the reverse direction and due to a corresponding movement or displacement of the protective membrane 26 and of the air or gas displacement means or generator 4 there is forced a gas mixture or reference gas which is at least partially free from reducing gases, through the connecting aperture 8 into the measuring chamber 7 and the reference gas leaves the measuring chamber 7 through the inlet opening 9 during the venting phase 29.

During this time period there occurs no or a much smaller additional heat of combustion at the gas sensor 11. Therefore, the gas sensor 11 assumes a slightly lower temperature during the venting phase 29 at the high temperature as well as at the low temperature as compared to the suction phase 28. The electrical conductivity $\sigma$ is thus generally higher during the venting phase 29.

The electrical conductivity $\sigma$ of the heater winding 10 is converted by means of the evaluation circuit arrangement 3 into a voltage signal which is measured at the points $A_3$, $A_4$, $B_3$ and $B_4$ as indicated in FIG. 4a, i.e. at the respective ends of each high-temperature section and of each low-temperature section of the heating cycle. The values $A_3$, $A_4$, $B_3$ and $B_4$ are delivered and stored and therefrom the differences $A_4-A_3$ and $B_4-B_3$ are formed. The ratio between the two differences $(A_4-A_3):(B_4-B_3)$ depends on the nature of the reducing gases which are present in the gas mixture to be investigated. Whenever the value $A_4-A_3$ which is a measure for the total concentration of reducing gases, exceeds a predetermined value, the evaluation circuit arrangement 3 generates an alarm signal and also determines from the aforementioned ratio the nature of the reducing gas. This additional information can be utilized for generating additional alarm signals, for example, when it is found that the detected reducing gas is also toxic which is the case, for example, when such reducing gas is carbon monoxide.

In comparison to the conventional pellistor principle which requires a measuring pellistor and a reference pellistor, the inventive gas detector 100 used for carrying out the inventive method comprises only a single pellistor which constitutes the gas sensor 11. Since the air or gas displacement means or generator 4 requires only very little electric power and since the pellistor is operated about half of the time at a low temperature, the presently described gas detector only has a power consumption which is about a third of that of conventional gas detectors which contain a pair of pellistors and which are continuously operated at high temperature. Since the differences $A_4-A_3$ and $B_4-B_3$ can be measured very precisely and are hardly effected by long-time variations or fluctuations of pressure, temperature and humidity, the presently described gas detector 100 reliably indicates even smallest concentrations of reducing gases in the gas mixture to be investigated which is in contrast to the conventional pellistor principle.

Figure 16:
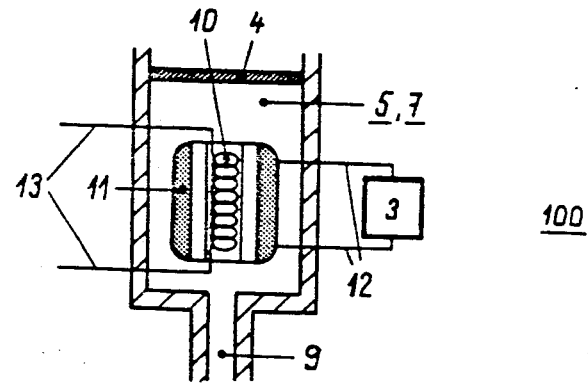
FIG. 16 is a schematic cross-sectional view of an eighth embodiment of the inventive apparatus.

An eighth embodiment of the inventive gas detector 100 for carrying out the inventive method is schematically illustrated in FIG. 16 in cross-sectional view. By virtue of its extremely simple construction such gas detector 100 is very well suited for mass production. The measuring chamber 7 and the reference chamber 5 directly merge with each other without a connecting aperture 8. Consequently, the gas sensor 11 including its heating means 10 is located within a chamber which simultaneously constitutes the measuring chamber 7 and the reference chamber 5. At least one wall or wall portion of this common chamber is constructed as an air or gas displacement means or generator 4.

When in the present embodiment a gas sensor 11 of the aforementioned type TGS-812 is used, the ratio of the volume of the measuring chamber, which is equal to the volume of the reference chamber, to the sum of the volumes of the gas sensor 11 and the heating means 10 has a value of about 5:1. According to the inventive method the presently described gas detector 100 generates the differences $A_2-A_1$ and $B_1-B_2$ by means of the evaluation circuit arrangement 3 and such differences are practically independent of changes in the temperature, in the pressure and in the relative humidity. Consequently, reducing gases can be measured with such gas detector 100 much more sensitively and trouble-free in comparison to any one of the hitherto usual gas sensors in which the absolute electrical conductivity $\sigma$ is directly used for detecting gases.

A ninth embodiment of the inventive gas detector 100 constitutes a further development of the gas detector 100 described hereinbefore with reference to FIG. 16. For better recognition of details the measuring chamber 7 in the presently illustrated embodiment is shown at an approximately 30 times larger scale than the reference chamber 5. The gas sensor 11 is made of a highly porous piece of a cubic metal oxide semiconductor having the dimensions $1 \times 1 \times 1$ mm$^3$ and such piece is provided with a central hole. The gas sensor 11 is provided with electrical lines 12 which are fixed to two electrodes 32 which are mounted on two sides of the cubic metal oxide semiconductor. The electrodes 32 serve for measuring the electrical conductivity $\sigma$ of the gas sensor 11. The heating means 10 are supplied with electrical power via supply lines or wires 13 and this electrical power is required to heat the gas sensor 11. The heating means 10 need not be mounted only on one side of the gas sensor 11, but can also uniformly heat the gas sensor 11 to a predetermined temperature on a greater number of sides thereof. In order to reduce heat conduction, the walls of the measuring chamber 7 and of the reference chamber 5 are preferably made of a thermally insulating, gas-tight material.

The gas sensor 11 fills the entire measuring chamber 7 with the exception of a small gap 37 at the periphery thereof. The measuring chamber 7 directly merges with the reference chamber 5 at the connecting aperture 8. The volume of the reference chamber 5 is periodically varied by means of the air or gas displacement means or generator 4. During movement or displacement of the air or gas displacement means or generator 4 the gas mixture to be investigated is periodically drawn through the inlet opening 9 and through the gas sensor 11 during the suction phase 28. Thereafter the gas mixture is blown off again in the reverse direction during the venting phase 29. Using the arrangement illustrated in FIG. 17 there is achieved an optimal conversion of the reducing gases which are contained in the gas mixture to be investigated. The ratio of the sum of the volumes of the gas sensor 11 and of the heating means 10 to the sum of the volumes of the measuring chamber 7 and of the reference chamber 5 is practically about 1:1.

Using a gas detector 100 of the presently described embodiment there could be measured even smallest traces of reducing gases at highest precision and at a power consumption of only about 25 mW of electrical power which is about 1/20 of the power required by hitherto used gas sensors which additionally are substantially less sensitive.

Figure 18:
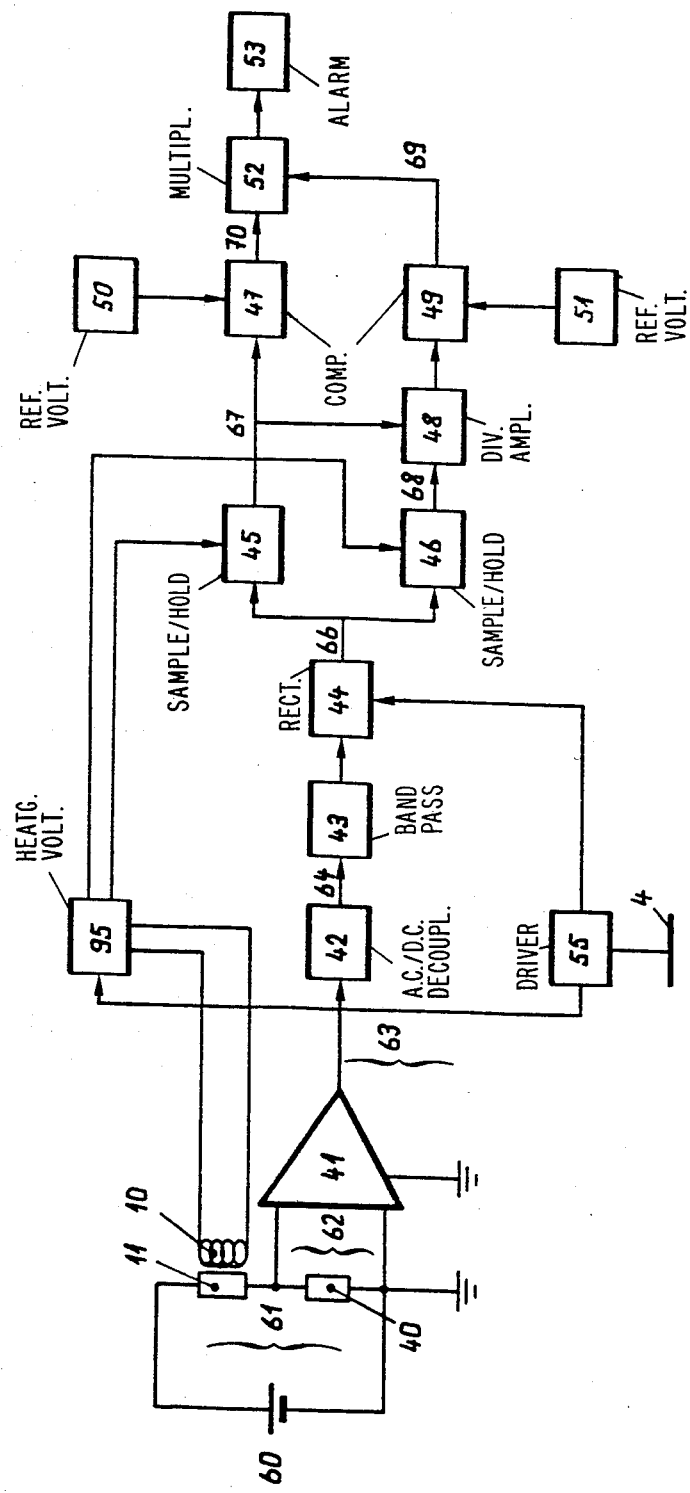
FIG. 18 is a schematic block circuit diagram of an evaluation circuit arrangement which can be used in combination with any one of the embodiments of the inventive apparatus illustrated in FIGS. 1, 2, 11 to 17, 21 and 22.

The processing and evaluation of the differences $A_2-A_1$ or solely $A_2$ and $B_1-B_2$ by means of the evaluation circuit arrangement 3 can be performed by any suitable electronic circuit arrangement. A suitable example is illustrated in FIG. 18 in the form of a schematic block circuit diagram and such evaluation circuit arrangement can be used in carrying out the inventive method illustrated in FIG. 3a to 3c.

The gas sensor 11 is series connected with a load resistor 40 and the measuring voltage 61 of the voltage source 60 is applied to this series connection. The voltage 62 is tapped from the load resistor 40 by an amplifier 41 and, by virtue of the specific amplification characteristic of the amplifier 41, the voltage 62 is converted into a voltage signal 63 which is proportional to the electrical conductivity $\sigma$ of the gas sensor 11. The amplifier 41 may also have a logarithmic characteristic since the inventive gas detector 100 in accordance with Equation (1) has a very large dynamic range for the occurring a.c.-signals 64. The voltage signal 63 is composed of a slowly varying d.c.-voltage component which is modulated by an a.c.-voltage component of the frequency of the air or gas displacement means or generator 4. By means of the a.c.- d.c.-decoupler 42 a pure a.c.-signal 64 is obtained, for example, by means of a suitably selected coupling capacitor. The a.c.-signal is advantageously filtered by means of a band-pass 43 and is converted by means of a rectifier 44 which may be, for example, a phase-selective rectifier, into a d.c.-voltage signal which is proportional to the amplitude 66 of the a.c.-signal. The rectifier 44 is controlled by the frequency of the driver unit 55 which drives the air or gas displacement means or generator 4.

The a.c.-amplitude 66 now varies between the values of the high temperature and of the low temperature of the gas sensor 11. The corresponding values are detected by two sample-and-hold units 45 and 46 of which the unit 45 measures a value 67 of the a.c.-amplitude at high temperatures and the unit 46 a value 68 of the a.c.-amplitude at low temperatures of the gas sensor 11. The required pulses for starting the sample-and-hold units are supplied by the heating voltage source 95 which, in turn, is synchronized with the driver unit 55. The values 67 and 68 are compared with each other in a divider amplifier 48 and the result of such division is compared in a comparator 49 with a reference value which is derived from a reference voltage source 51. When the ratio of the value 67 to the value 68 corresponds to a value related to a dangerous gas, the comparator 49 generates a voltage 69 corresponding to a logic 1, otherwise the voltage 69 corresponds to a logic zero. When the value 67 exceeds a reference value supplied by a voltage source 50, the comparator 47 generates a signal 70 having the logic value 1 and this signal 70 is multiplied with the logic signal 69 in a multiplier 52. In the case that both signals 69 and 70 correspond to a logic 1, an alarm circuit 53 is activated.

Figure 19:
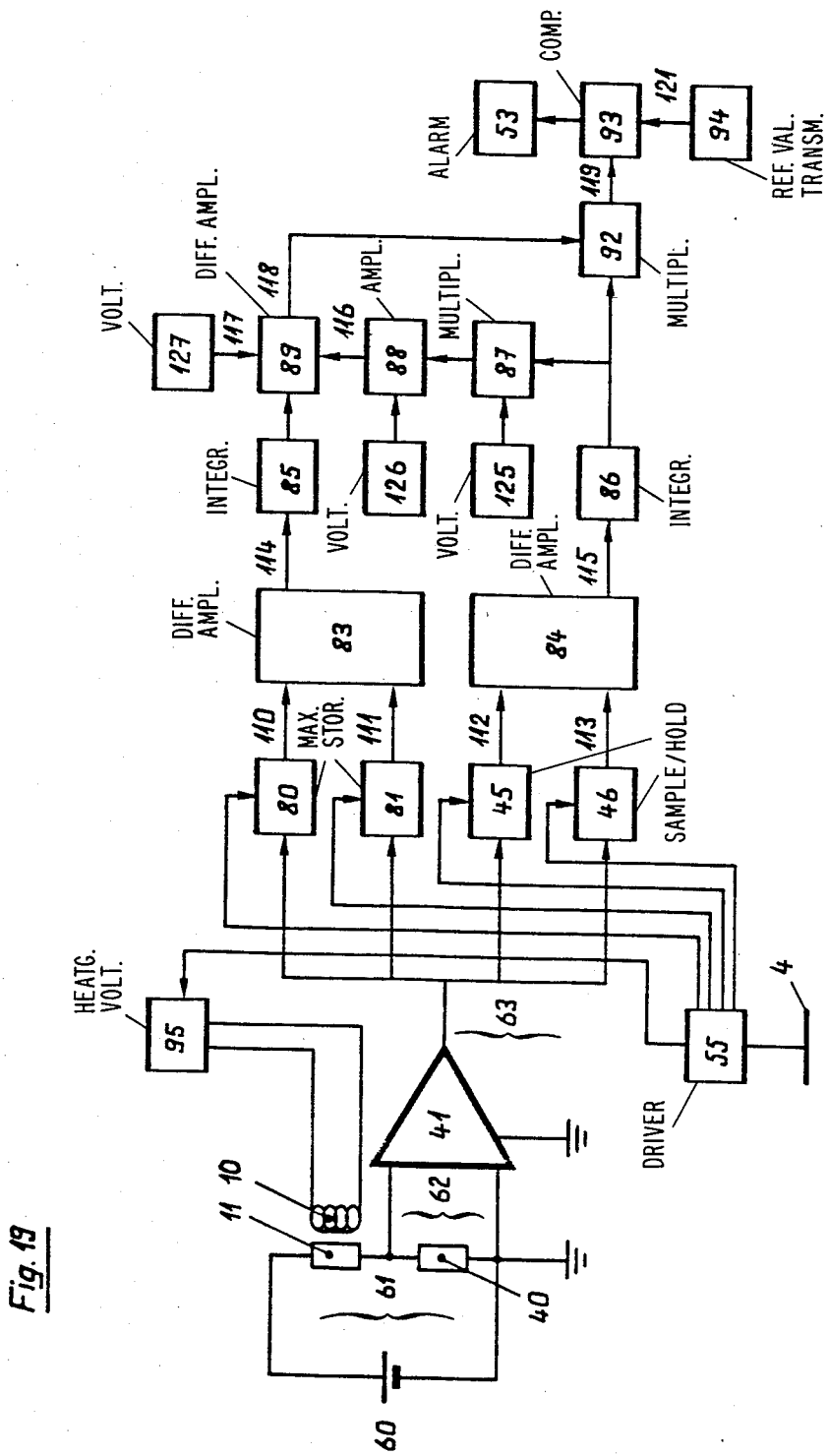
FIG. 19 is a schematic block circuit diagram of a further evaluation circuit arrangement which can be used in combination with any one of the embodiments of the inventive apparatus illustrated in FIGS. 1, 2, 11 to 17, 21 and 22.

A further electronic circuit arrangement is illustrated in FIG. 19 and such electronic circuit arrangement can be used in carrying out the inventive method illustrated in FIGS. 4a to 4c and 5a to 5c. The gas sensor circuit comprises the gas sensor 11, the load resistor 40 and the voltage source 60 which generates the voltage 61 and generates the voltage 62. This signal is processed by the amplifier 41 which delivers a voltage signal 63. This voltage signal 63, on the one hand, is supplied to the two sample-and-hold units 45 and 46. The moment of time of the measurement is determined by the driver unit 55 which drives the air or gas displacement means or generator 4 and which runs synchronously with the heating voltage source 95, in such a manner that the sample-and-hold unit 45 measures the value $B_1$ and the sample-and-hold unit 46 measures the value $B_2$. Also, the sample-and-hold units 45 and 46 supply voltages 112 and 113 which are proportional to the values $B_1$ and $B_2$, respectively. The voltage signal 63, on the other hand, is supplied to two maximum value storages 80 and 81 which measure the maximum value of the voltage signal 63 during a time interval determined by the driver unit 55. The maximum value storages 80 and 81 supply voltages 110 and 111, respectively, which correspond to the maximum values $A_1$ and $A_2$, respectively, shown in FIG. 4a.

When a pellistor is used instead of the semiconductor gas sensor for the gas sensor 11, the maximum value storages 80 and 81 are replaced by sample-and-hold units which are analogous to the sample-and-hold units 45 and 46.

The voltages 110 and 111 are converted in the differential amplifier 83 to form a voltage 114 which is proportional to the difference $A_2-A_1$ and which is smoothed by means of an integrator 85. The voltages 112 and 113 are converted in a differential amplifier 84 to form a voltage 115 which corresponds to the difference $B_1-B_2$ and which is smoothed by an integrator 86.

In a multiplier 87 and an addition amplifier 88 the smoothed voltage 115 produces conjointly with voltages 125 and 126, which correspond to the values a and b, respectively, in Equation (3) given hereinbelow, a fictitious value 116 of the difference $A_2-A_1$. The multiplier 87 and the addition amplifier 88 operate according to Equation (3)

$$\text{fictitious } (A_2-A_1) \text{ Value}=a\cdot(B_1-B_2)+b \qquad \text{Equation (3),}$$

wherein the two constants a and b describe a straight line which has been optimally matched by regressional computation to the slightly curved broken line for carbon monoxide in FIG. 7. The constant a designates the slope of the straight line and the constant b designates the ordinate intercept. This straight line extends approximately at the middle between the measured values for a very humid atmosphere and a very dry atmosphere. The fictitious $A_2-A_1$ value 116 lies approximately on this broken line in FIG. 7. The fictitious $A_2-A_1$ value 116 is subtracted from the measured and smoothed $A_2-A_1$ value 114 in a differential amplifier 89. When the fictitious and the true $A_2-A_1$ values coincide within the limits shown in FIG. 7 for alternating relative humidities and for carbon monoxide, the presence of solely carbon monoxide as a reducing gas in the gas mixture to be investigated is clearly demonstrated.

The differential amplifier 89 forms the negative absolute value of the difference (voltage 116−voltage 114). There is added thereto a voltage 117 which is generated by a voltage source 127 and which corresponds to the ordinate-parallel distance k in FIG. 7 between the bands for carbon monoxide and methane. There is thus generated by the differential amplifier 89 a voltage 118 which corresponds to the value: k−|true $(A_2-A_1)$ value−fictitious $(A_2-A_1)$ value|. The smoothed voltage 115 is multiplied with the voltage 118 in a multiplier 92. When the fictitious and the true $(A_2-A_1)$ values coincide, the multiplication in the multiplier 92 is by the factor k. When the fictitious value 116 and the true value 114 of the difference $A_2-A_1$ do not coincide within the limits for carbon monoxide shown in FIG. 7, the change in the electrical conductivity $\sigma$ observed at the gas sensor 11 obviously is not only due to the dangerous carbon monoxide, but is also and additionally due to methane. In such case the differential amplifier 89 generates a voltage 118 which multiplies the smoothed voltage 115 in the multiplier 92 by a factor having a value in the range of zero to k. The output voltage 119 of the multiplier 92 now corresponds to a value of the difference $B_1-B_2$ which is solely due to carbon monoxide.

The comparator 93 compares this "only-carbon monoxide-$(B_1-B_2)$-value" 119 with a reference voltage 121 of a reference value transmitter 94 and activates an alarm circuit 53 whenever the aforementioned value 119 exceeds a predetermined threshold value. When the bands for the gases carbon monoxide and methane do not extend parallel to each other in a representation corresponding to FIG. 7, the constant k becomes dependent upon the value of the difference $B_1-B_2$. Consequently, a further multiplier amplifier, not particularly illustrated in FIG. 19, is provided in order to correct the constant k in correspondence with the value of the difference $B_1-B_2$. This can be conveniently done by affecting the voltage source 127.

When only $A_2$ is used instead of the difference $A_2-A_1$, the maximum value storage 80 and the differential amplifier 83 can be omitted. When the bands for carbon monoxide and methane in a representation corresponding to FIG. 7 can not be approximated sufficiently precisely by straight lines, the curves shown in broken lines in FIG. 7 are represented by a general polynomial of the nth degree. Therefore, there are now required n+1 voltages instead of the two voltages 125 and 126 and there is also required a correspondingly higher number of addition amplifiers and multiplication amplifiers.

The evaluation circuit arrangement described hereinbefore with reference to FIG. 19 can also be used in such a manner that only the presence of one specific reducing gas present with other reducing gases is indicated by suitable optical or acoustic means.

Figure 20:
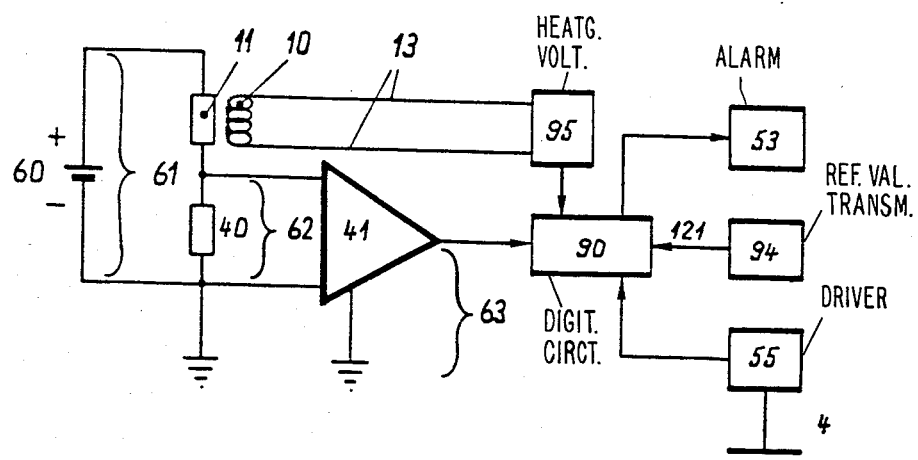
FIG. 20 is a schematic block circuit diagram of an evaluation circuit arrangement which can be used in combination with any one of the embodiments of the inventive apparatus illustrated in FIGS. 1, 2, 11 to 17, 21 and 22.

The functions described hereinbefore with reference to FIGS. 18 and 19, of course, can not only be provided by analog circuitry in conventional manner, but can also be realized by digital circuits in combination with the use of a microprocessor, all of which are known to a person skilled in the art. A related block circuit diagram is shown in FIG. 20. The voltage signal 63 processed by the amplifier 41 is in the present case digitized in known manner by means of a digital circuit 90 containing a microprocessor. Advantageously, the sampling frequency is at least 2, better 10 and specifically 100 times higher than the frequency of the air or gas displacement means or generator 4, the frequency of the driver unit 55 thereof, and of the frequency of the temperature or heating cycles, which are made available to the digital circuit 90 as reference frequencies. In comparison to the reference voltage 121 of the reference value transmitter 94 the digital circuit 90 computes and determines whether a predetermined reducing gas is present in dangerous concentration and, if desired, activates an alarm circuit 53.

The circuit arrangement shown in FIGS. 19 and 20 analogously can be used for determining and evaluating the differences $A_4-A_3$ and $B_4-B_3$ shown in FIG. 4a, when a pellistor is used as the gas sensor 11.

Figure 21:
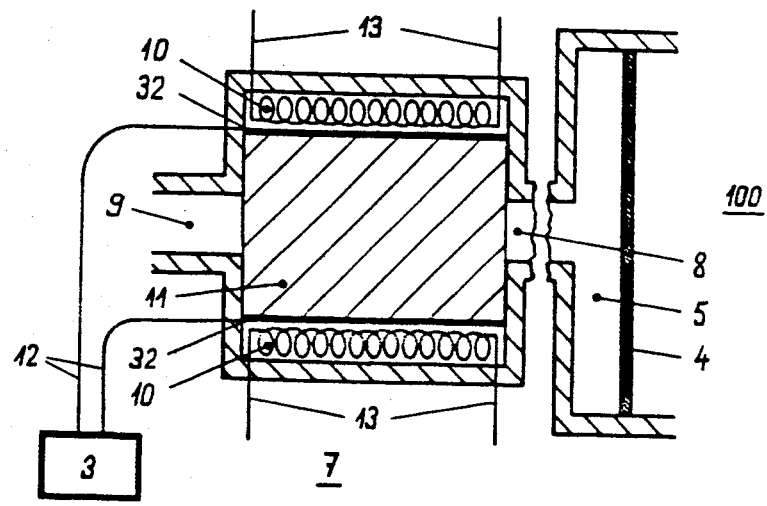
FIG. 21 is a schematic cross-sectional view of a tenth embodiment of the inventive apparatus.

FIG. 21 shows a tenth embodiment of the inventive gas detector 100 in a schematic and cross-sectional view. For better recognizability of the details, the measuring chamber 7 is shown at an approximately thirty times greater scale than the reference chamber 5. The gas sensor 11 has the dimensions $0.8 \times 0.8 \times 0.5$ mm$^3$ and is formed by a piece of highly porous metal oxide carrying the electrodes 32 on two sides thereof. The gas sensor 11 is heated by two heating means 10 to a predetermined temperature. The gas sensor 11 completely fills the measuring chamber 7.

The air or gas displacement means or generator 4 forms a wall or a wall portion of the reference chamber 5 and is formed by a metal membrane having a diameter of 30 mm. This metal membrane is driven by a commercially available piezo oscillator. The small movement or displacement amplitudes thereof are sufficient to draw the gas mixture to be investigated through the inlet opening 9, through the gas sensor 11, and through the connecting aperture 8 into the reference chamber 5 and to subsequently vent or blow out again the gas mixture in the reverse direction from the reference chamber 5 through the connecting aperture 8 and the gas sensor 11 and the inlet opening 9.

The walls of the measuring chamber 7 and of the reference chamber 5 are made of a gas-tight material having a very low heat conductivity. Therefore, this gas detector 100 requires only about 80 mW of electric power. The gas detector 100 of the presently described embodiment can extremely precisely detect even smallest traces of reducing gases by measuring the electrical conductivity $\sigma$ of the gas sensor 11 by means of the electrodes 32, the supply lines 12 and the evaluation circuit arrangement 3. The measured values are converted into the differences $B_1-B_2$ and $A_2-A_1$. By a comparison of the two differences the evaluation circuit arrangement 3 additionally can determine which reducing gas has been detected. When the gas detector 100 is intended to determine the concentration of a specific reducing gas, this is also possible since the evaluation circuit arrangement 3 of the kind as illustrated in the block circuit diagrams of FIGS. 18 to 20 automatically perform the computations and conversions required therefor. This determination of concentration is independent of whether there are other reducing gases present in the gas mixture to be investigated in addition to the gas specially to be detected.

The ratio of the reference chamber volume to the measuring chamber volume amounts to approximately 5:1. The ratio of the sum of the volumes of the reference chamber 5 and of the measuring chamber 7 to the sum of the volumes of the gas sensor 11 and of the heating means 10 amounts to approximately 6:1 for this gas detector 100 which has been experimentally tested.

Figure 17:
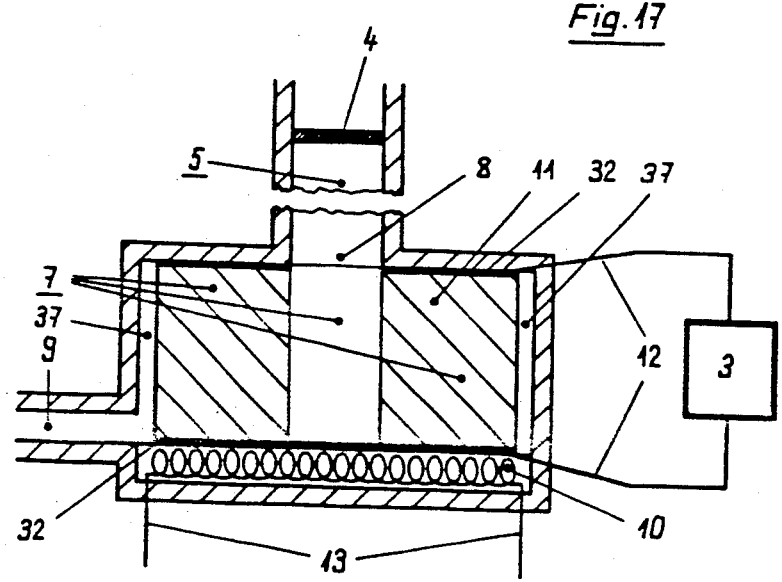
FIG. 17 is a schematic cross-sectional view of a ninth embodiment of the inventive apparatus.

A further development of the gas detector 100 illustrated in FIG. 17 is shown in a schematic and perspective view in FIG. 22. The gas sensor 11 therein consists of a quadrangularly shaped piece of metal oxide at which the electrodes 32 are mounted at two opposite sides. In this design the material of the gas sensor constitutes the measuring chamber 7. The porous metal oxide may constitute a material as described in the commonly assigned, copending U.S. application Ser. No. 06/586,329, filed Mar. 5, 1984, and as described in the commonly assigned, copending U.S. applications Ser. Nos. 06/633,652 and 06/635,881 which have been initially cross-referenced. The measuring chamber 7, i.e. the metal oxide block, has the dimensions $2 \times 2 \times 1$ mm$^3$ and in the illustrated design the electrodes 32 form the bottom side and the top side of the measuring chamber 7. The side walls of the metal oxide block define the inlet opening 9, i.e. the connection to the external or environmental atmosphere. Due to this structure there is ensured an extremely rapid gas exchange and the flow resistance of the gas sensor 11 is held at a minimum. The reference chamber 5 is immediately set upon one of the two electrodes 32. The connecting aperture 8 is located within this electrode 32. The air or gas displacement means or generator 4 at the end of the reference chamber 5 is a mini-loudspeaker having a diameter of about 20 mm and the reference chamber 5 constitutes a tube made of a material having low heat conductivity.

Due to the movement or displacements of the air or gas displacement means or generator 4, the gas mixture to be investigated is drawn through the walls and the material of the gas sensor 11 and thus through the measuring chamber 7 into the reference chamber 5 and subsequently is vented or blown off in the reverse direction. The heating means 10 is mounted at a thermally insulating support 38. There are thus required only about 250 mW of electrical heating power. Even smallest traces of reducing gases can be detected by means of this gas detector 100. The electrical output signals are processed in an evaluation circuit arrangement of the type as described hereinbefore.

This construction has the advantage that the volume of the measuring chamber 7 is exactly defined by the volume of the gas sensor 11. Due to this construction there is obtained a high reproducibility of the a.c.-voltage signals and the d.c.-voltage signals for different gas detectors 100.

While there are shown and described present preferred embodiments of the invention, it is to be distinctly understood that the invention is not limited thereto, but may be otherwise variously embodied and practiced within the scope of the following claims.

Accordingly, what we claim is:

1. A method of detecting at least one reducing gas in a gas mixture to be investigated, particularly in air, said method comprising the steps of:
    selecting a gas sensor containing a metal oxide semiconductor possessing a selected property which is dependent on the presence of said at least one reducing gas in said gas mixture;
    cyclically varying the temperature of said gas sensor by continuously increasing said temperature from a starting value to an upper threshold value and subsequently decreasing said temperature from said upper threshold value to said starting value;
    cyclically exposing said gas sensor to said gas mixture to be investigated and at least partially to a reference gas containing a smaller amount or none of said at least one reducing gas, whereby said selected property of said metal oxide semiconductor is subject to a cyclical variation as a function of time; and
    measuring said cyclical variation of said selected property of said metal oxide semiconductor.

2. The method as defined in claim 1, wherein:
    said step of selecting said gas sensor entails selecting a gas sensor containing a metal oxide semiconductor which possesses an optical transmission in a preselected spectral range and which optical transmission is dependent on the presence of said at least one reducing gas in said gas mixture to be investigated.

3. The method as defined in claim 1, wherein:
    said step of selecting said gas sensor entails the step of selecting a gas sensor containing a metal oxide semiconductor which possesses as the selected property an electrical property which is dependent on the presence of said at least one reducing gas in said gas mixture to be investigated.

4. The method as defined in claim 3, wherein:
    said step of selecting said gas sensor entails selecting a gas sensor containing a metal oxide semiconductor which possesses as the selected property an electrical conductivity which is dependent on the presence of said at least one reducing gas in said gas mixture to be investigated.

5. The method as defined in claim 3, wherein:
    said step of selecting said gas sensor entails selecting a gas sensor containing a metal oxide semiconductor which possesses as the selected property an electrical resistance dependent on the presence of said at least one reducing gas in said gas mixture to be investigated.

6. The method as defined in claim 1, wherein:
    said step of cyclically varying the temperature of said gas sensor includes the step of cyclically varying said temperature of said gas sensor through at least two temperature cycles, each of which comprises continuously increasing said temperature from a starting value to an upper threshold value and subsequently decreasing said temperature from said upper threshold value to said starting value.

7. The method as defined in claim 1, wherein:
    said step of cyclically varying said temperature of said gas sensor includes continuously increasing said temperature from said starting value to said upper threshold value in accordance with a predetermined pattern.

8. The method as defined in claim 1, wherein:
    said step of cyclically varying said temperature of said gas sensor includes continuously decreasing said temperature from said upper threshold value to said starting value in accordance with a further predetermined pattern.

9. The method as defined in claim 8, further including the step of:
    selecting as said further predetermined pattern a pattern which is different from said predetermined pattern according to which said temperature is continuously increased from said starting value to said upper threshold value.

10. The method as defined in claim 8, further including:
    selecting as said further predetermined pattern a pattern which substantially is the reversal of said predetermined pattern according to which said temperature is continuously increased from said starting value to said upper threshold value.

11. The method as defined in claim 1, wherein:
    said step of measuring said cyclical variation of said selected property of said metal oxide semiconductor entails detecting the presence of said at least one reducing gas in said gas mixture to be investigated.

12. The method as defined in claim 1, wherein:
    said step of measuring said cyclical variation of said selected property of said metal oxide semiconductor entails identifying the nature of said at least one reducing gas in said gas mixture to be investigated.

13. The method as defined in claim 1, wherein:
    said step of selecting said gas sensor entails selecting a gas sensor containing a metal oxide semiconductor which possesses as said selected property a property which is directly dependent on the concentration of said at least on reducing gas in said gas mixture to be investigated; and
    said step of measuring said cyclical variation of said selected property of said metal oxide semiconductor entails determining the concentration of said at least reducing gas in said gas mixture to be investigated.

14. The method as defined in claim 1, further including the steps of:
- selecting as said gas sensor a gas sensor containing a metal oxide semiconductor which is capable of effecting a conversion of said at least one reducing gas to an inactive component which has no or only a negligible affect on said selected property of said metal oxide semiconductor and which thus converts said gas mixture into a reference gas;
- arranging said gas sensor in a measuring chamber having an inlet opening;
- providing a reference chamber of a variable volume and which reference chamber contains said reference gas, is closed to the external atmosphere and is provided with gas displacement means;
- further connecting said measuring chamber through at least one connecting aperture to said reference chamber;
- said step of cyclically exposing said gas sensor to said gas mixture to be investigated and to said reference gas entails periodically exchanging the gas which is present in said measuring chamber by cyclically operating said gas displacement means; and
- said step of cyclically operating said gas displacement means including:
  - (i) during a suction phase of said cyclic operation of said gas displacement means increasing said variable volume of said reference chamber;
  - (ii) admitting said gas mixture to be investigated into said measuring chamber through said inlet opening thereof;
  - (iii) at least partially removing said at least one reducing gas from said gas mixture to be investigated by means of said gas sensor and thereby forming said reference gas containing less or none of said at least one reducing gas;
  - (iv) drawing said reference gas into said reference chamber through said at least one connecting aperture;
- said step of cyclically operating said gas displacement means further includes, during a venting phase of said cyclic operation of said gas displacement means;
  - (i) decreasing said variable volume of said reference chamber; and
  - (ii) venting said reference gas and blowing the same off through said measuring chamber and said inlet opening thereof; and
- said step of measuring said cyclic variation of said selected property of said metal oxide semiconductor of said gas sensor entails measuring said cyclic variation due to said cyclic operation of said gas displacement means.

15. The method as defined in claim 14, wherein:
- said step of measuring said cyclic variation due to said cyclic operation of said gas displacement means entails detecting the presence of said at least one reducing gas in said gas mixture to be investigated.

16. The method as defined in claim 14, wherein:
- said step of measuring said cyclic variation due to said cyclic operation of said gas displacement means entails identifying the nature of said at least one reducing gas in said gas mixture to be investigated.

17. The method as defined in claim 14, wherein:
- said step of measuring said cyclic variation due to said cyclic operation of said gas displacement means entails determining the concentration of said at least one reducing gas in said gas mixture to be investigated.

18. The method as defined in claim 14, wherein:
- said step of measuring said cyclic variation of said selected property of said metal oxide semiconductor includes measuring a modulated, cyclically varying signal composed of a first signal component which varies slowly with time depending on said cyclic temperature variation, and a second signal component which is modulated in correspondence with said periodic gas exchange and changes its sign;
- said step of measuring said cyclic variation of said selected property of said metal oxide semiconductor further including the steps of:
- separating said first signal component from said second signal component;
- converting said first signal component into a slowly varying d.c.-signal; and
- converting said second signal component into an a.c.-signal having a predetermined amplitude and determining at least said amplitude of said a.c.-signal in order to detect said at least one reducing gas in said gas mixture to be investigated.

19. The method as defined in claim 14, further including the steps of:
- selecting for said gas exchange period encompassing said suction phase and said venting phase, a predetermined duration;
- selecting a heating cycle of a predetermined duration for said step of cyclically varying the temperature of said gas sensor;
- selecting as said predetermined duration of said gas exchange period a duration which is substantially equal to twice the predetermined duration of said heating cycle;
- maintaining said gas sensor at a first temperature during a high temperature section of said heating cycle and during a first part of said suction phase of said gas exchange period;
- maintaining said gas sensor at a second temperature during a low-temperature section subsequent to said high-temperature section of said heating cycle and during a second part of said suction phase of said gas exchange period;
- maintaining said gas sensor at a third temperature during a high-temperature section of said heating cycle and during a first part of said venting phase of said gas exchange period;
- maintaining said gas sensor at a fourth temperature during a low-temperature section subsequent to said high-temperature section of said heating cycle and during a second part of said venting phase of said gas exchange period;
- measuring maximum values of said selected property of said metal oxide semiconductor of said gas sensor during said high-temperature section of said heating cycle during said suction phase and during said venting phase of said gas exchange period; and
- measuring at least one value of said selected property of said metal oxide semiconductor of said gas sensor substantially at the end of said low-temperature section of said heating cycle during said suction phase of said gas exchange period.

20. The method as defined in claim 19, further including the step of:

additionally measuring a further value of said selected property of said metal oxide semiconductor of said gas sensor substantially at the end of said low-temperature section of said heating cycle during said venting phase of said gas exchange period.

21. The method as defined in claim 19, further including the step of:
detecting the presence of said at least one reducing gas in said mixture to be investigated by means of said measured maximum values and said at least one measured value of said selected property of said metal oxide semiconductor of said gas sensor.

22. The method as defined in claim 19, further including the step of:
identifying the nature of said at least one reducing gas in said gas mixture to be investigated by means of said measured maximum values and said at least one measured value of said selected property of said metal oxide semiconductor of said gas sensor.

23. The method as defined in claim 19, further including the step of:
determining the concentration of said at least one reducing gas in said gas mixture to be investigated by means of said measured maximum values and said at least one measured value of said selected property of said metal oxide semiconductor of said gas sensor.

24. The method as defined in claim 19, further including the step of:
selecting as said first temperature at which said gas sensor is maintained during said high-temperature section of said heating cycle during said suction phase of said gas exchange period, a temperature which is higher by at least 50° C. than said second temperature at which said gas sensor is maintained during said low-temperature section of said heating cycle.

25. The method as defined in claim 24, further including the step of:
selecting as said first temperature a temperature of about 350° C.

26. The method as defined in claim 19, further including the step of:
selecting as said second temperature at which said gas sensor is maintained during said low-temperature section of said heating cycle during said suction phase of said gas exchange period, a temperature in the range of about 30° C. to about 300° C.

27. The method as defined in claim 26, further including the step of:
selecting as said second temperature a temperature of about 50° C.

28. The method as defined in claim 19, further including the step of:
selecting as said third temperature at which said gas sensor is maintained during said high-temperature section of said heating cycle during said venting phase of said gas exchange period, a temperature which is higher by at least 50° C. than said fourth temperature at which said gas sensor is maintained during said low-temperature section of said heating cycle.

29. The method as defined in claim 28, further including the step of:
selecting as said third temperature a temperature of about 350° C.

30. The method as defined in claim 19, further including the step of:
selecting as said fourth temperature at which said gas sensor is maintained during said low-temperature section of said heating cycle during said venting phase of said gas exchange period, a temperature which is in the range of about 30° C. to about 300° C.

31. The method as defined in claim 30, further including the step of:
selecting as said fourth temperature a temperature of about 50° C.

32. The method as defined in claim 1, further including the steps of:
selecting for said gas exchange period encompassing said suction phase and said venting phase, a predetermined duration;
selecting a heating cycle of a predetermined duration for said step of cyclically varying the temperature of said gas sensor;
selecting as said predetermined duration of said gas exchange period a duration which is substantially equal to twice the predetermined duration of said heating cycle;
maintaining said gas sensor at a first temperature during a low-temperature section of said heating cycle and during a first part of said suction phase of said gas exchange period;
maintaining said gas sensor at a second temperature during a high-temperature section subsequent to said low-temperature section of said heating cycle and during a second part of said suction phase of said gas exchange period;
maintaining said gas sensor at a third temperature during a low-temperature section of said heating cycle and during a first part of said venting phase of said gas exchange period;
maintaining said gas sensor at a fourth temperature during a high-temperature section subsequent to said low-temperature section of said heating cycle and during a second part of said venting phase of said gas exchange period;
measuring maximum values of said selected property of said metal oxide semiconductor of said gas sensor during said high-temperature sections of said heating cycle during said suction phase and during said venting phase of said gas exchange period; and
measuring at least one value of said selected property of said metal oxide semiconductor of said gas sensor substantially at the end of said low-temperature section of said heating cycle during said suction phase of said gas exchange period.

33. The method as defined in claim 32, further including the step of:
additionally measuring a further value of said selected property of said metal oxide semiconductor of said gas sensor substantially at the end of said low-temperature section of said heating cycle during said venting phase of said gas exchange period.

34. The method as defined in claim 32, further including the step of:
detecting the presence of said at least one reducing gas in said mixture to be investigated by means of said measured maximum values and said at least one measured value of said selected property of said metal oxide semiconductor of said gas sensor.

35. The method as defined in claim 32, further including the step of:
identifying the nature of said at least one reducing gas in said gas mixture to be investigated by means of said measured maximum values and said at least one measured value of said selected property of said metal oxide semiconductor of said gas sensor.

36. The method as defined in claim 32, further including the step of:

determining the concentration of said at least one reducing gas in said gas mixture to be investigated by means of said measured maximum values and said at least one measured value of said selected property of said metal oxide semiconductor of said gas sensor.

37. The method as defined in claim 32, further including the step of:

selecting as said first temperature at which said gas sensor is maintained during said low-temperature section of said heating cycle during said suction phase of said gas exchange period a temperature in the range of about 30° C. to about 300° C.

38. The method as defined in claim 37, further including the step of:

selecting as said first temperature a temperature of about 50° C.

39. The method as defined in claim 32, further including the step of:

selecting as said second temperature at which said gas sensor is maintained during said high-temperature section of said heating cycle during said suction phase of said gas exchange period a temperature which is higher by at least 50° C. than said first temperature at which said gas sensor is maintained during said low-temperature section of said heating cycle.

40. The method as defined in claim 39, further including the step of:

selecting as said second temperature a temperature of about 350° C.

41. The method as defined in claim 32, further including the step of:

selecting as said third temperature at which said gas sensor is maintained during said low-temperature section of said heating cycle during said venting phase of said gas exchange period a temperature which is in the range of about 30° C. to about 300° C.

42. The method as defined in claim 41, further including the step of:

selecting as said third temperature a temperature of about 50° C.

43. The method as defined in claim 32, further including the step of:

selecting as said fourth temperature at which said gas sensor is maintained during said high-temperature section of said heating cycle during said venting phase of said gas exchange period a temperature which is higher by at least 50° C. than said third temperature at which said gas sensor is maintained during said low-temperature section of said heating cycle.

44. The method as defined in claim 43, further including the step of:

selecting as said fourth temperature a temperature of about 350° C.

45. The method as defined in claim 14, further including the steps of:

selecting for said gas exchange period encompassing said suction phase and said venting phase a predetermined duration;

selecting a heating cycle of a predetermined duration for said step of cyclically varying the temperature of said gas sensor; and selecting for said gas exchange period a predetermined duration which is different from twice said predetermined duration of said heating cycle.

46. The method as defined in claim 45, wherein:

said step of selecting said predetermined duration for said gas exchange period entails selecting a duration which is shorter than twice said predetermined duration of said heating cycle.

47. The method as defined in claim 20, further including the steps of:

determining a difference between said measured value and said measured further value of said selected property of said metal oxide semiconductor of said gas sensor by subtracting said further value measured close to the end of said low-temperature section during said venting phase of said gas exchange period from said value measured close to said end of said low-temperature section during said suction phase of said gas exchange period; and detecting the presence of said at least one reducing gas in said gas mixture to be investigated by means of said difference determined between said value and said further value of said selected property of said metal oxide semiconductor measured during said low-temperature sections of said heating cycle.

48. The method as defined in claim 20, further including the steps of:

determining a difference between said measured value and said measured further value of said selected property of said metal oxide semiconductor of said gas sensor by subtracting said further value measured close to said end of said low-temperature section of said heating cycle during said venting phase of said gas exchange period from said value measured close to said end of said low-temperature section of said heating cycle during said suction phase of said gas exchange period; and determining the concentration of said at least one reducing gas in said gas mixture to be investigated by means of said difference determined between said value and said further value of said selected property of said metal oxide semiconductor measured during said low-temperature sections of said heating cycle.

49. The method as defined in claim 33, further including the steps of:

determining a difference between said measured value and said measured further value of said selected property of said metal oxide semiconductor of said gas sensor by subtracting said further value measured close to the end of said low-temperature section during said venting phase of said gas exchange period from said value measured close to said end of said low-temperature section during said suction phase of said gas exchange period; and detecting the presence of said at least one reducing gas in said gas mixture to be investigated by means of said difference determined between said value and said further value of said selected property of said metal oxide semiconductor measured during said low-temperature sections of said heating cycle.

50. The method as defined in claim 33, further including the steps of:

determining a difference between said measured value and said measured further value of said selected property of said metal oxide semiconductor of said gas sensor by subtracting said further value measured close to said end of said low-temperature section of said heating cycle during said venting phase of said gas exchange period from said value measured close to said end of said low-temperature section of said heating cycle during said suction phase of said gas exchange period; and determining the concentration of said at least one reducing gas in said gas mixture to be investigated by means of said difference determined between said value and said further value of said selected property of said metal oxide semiconductor measured during said low-temperature sections of said heating cycle.

51. The method as defined in claim 19, further including the steps of:

determining the difference between said maximum values of said selected property of said metal oxide semiconductor of said gas sensor by subtracting the maximum value measured during said high-temperature section of said heating cycle during said venting phase of said gas exchange period from said maximum value measured during said high-temperature section of said heating cycle during said suction phase of said gas exchange period; and detecting the presence of said at least one reducing gas in said gas mixture to be investigated by means of said difference determined between said maximum values of said selected property of said metal oxide semiconductor.

52. The method as defined in claim 19, further including the steps of:

determining the difference between said maximum values of said selected property of said metal oxide semiconductor of said gas sensor by subtracting the maximum value measured during said high-temperature section of said heating cycle during said venting phase of said gas exchange period from said maximum value measured during said high-temperature section of said heating cycle during said suction phase of said gas exchange period; and determining the concentration of said at least one reducing gas in said gas mixture to be investigated by means of said difference determined between said maximum values of said selected property of said metal oxide semiconductor.

53. The method as defined in claim 32, further including the steps of:

determining the difference between said maximum values of said selected property of said metal oxide semiconductor of said gas sensor by subtracting the maximum value measured during said high-temperature section of said heating cycle during said venting phase of said gas exchange period from said maximum value measured during said high-temperature section of said heating cycle during said suction phase of said gas exchange period; and detecting the presence of said at least one reducing gas in said gas mixture to be investigated by means of said difference determined between said maximum values of said selected property of said metal oxide semiconductor.

54. The method as defined in claim 32, further including the steps of:

determining the difference between said maximum values of said selected property of said metal oxide semiconductor of said gas sensor by subtracting the maximum value measured during said high-temperature section of said heating cycle during said venting phase of said gas exchange period from said maximum value measured during said high-temperature section of said heating cycle during said suction phase of said gas exchange period; and determining the concentration of said at least one reducing gas in said gas mixture to be investigated by means of said difference determined between said maximum values of said selected property of said metal oxide semiconductor.

55. The method as defined in claim 19, further including the steps of:

additionally measuring a further value of said selected property of said metal oxide semiconductor of said gas sensor substantially at the end of said low-temperature section of said heating cycle during said venting phase of said gas exchange period;

determining a difference between said value and said further value of said selected property of said metal oxide semiconductor by subtracting said further value measured close to said end of said low-temperature section of said heating cycle during said venting phase of said gas exchange period from said value measured close to said end of said low-temperature section of said heating cycle during said suction phase of said gas exchange period;

by means of said determined difference, detecting the presence and/or determining the concentration of said at least one reducing gas in said gas mixture to be investigated;

determining a difference between said maximum values of said selected property of said metal oxide semiconductor by subtracting the maximum value measured during said high-temperature section of said heating cycle during said suction phase of said gas exchange period from the maximum value measured during said high-temperature section of said heating cycle during said venting phase of said gas exchange period; and comparing said difference determined between said maximum values and said difference determined between said value and said further value in order to identify said at least one reducing gas in said gas mixture to be investigated.

56. The method as defined in claim 19, further including the steps of:

additionally measuring a further value of said selected property of said metal oxide semiconductor of said gas sensor substantially at the end of said low-temperature section of said heating cycle during said venting phase of said gas exchange period;

determining a difference between said value and said further value of said selected property of said metal oxide semiconductor by subtracting said further value measured close to said end of said low-temperature section of said heating cycle during said venting phase of said gas exchange period from said value measured close to said end of said low-temperature section of said heating cycle during said suction phase of said gas exchange period;

by means of said determined difference, detecting the presence and/or determining the concentration of said at least one reducing gas in said gas mixture to be investigated; and comparing said maximum value of said selected property of said metal oxide semiconductor and measured during said high-temperature section of said heating cycle during said suction phase of said gas exchange period with said determined difference in order to identify the nature of said at least one reducing gas in said gas mixture to be investigated.

57. The method as defined in claim 19, further including the steps of:

additionally measuring a further value of said selected property of said metal oxide semiconductor of said gas sensor substantially at the end of said low-temperature section of said heating cycle during said venting phase of said gas exchange period;

determining a difference between said measured value and said measured further value of said selected property of said metal oxide semiconductor by subtracting said further value measured close to said end of said low-temperature section of said heating cycle during said venting phase of said gas exchange period from said value measured close to said end of said low-temperature section of said heating cycle during said suction phase of said gas exchange period;

by means of said determined difference, detecting the presence and/or determining the concentration of said at least one reducing gas in said gas mixture to be investigated; and comparing said maximum value of said selected property of said metal oxide semiconductor and measured during said high-temperature section of said heating cycle during said venting phase of said gas exchange period with said determined difference in order to identify the nature of said at least one reducing gas in said gas mixture to be investigated.

58. The method as defined in claim 32, further including the steps of:

additionally measuring a further value of said selected property of said metal oxide semiconductor of said gas sensor substantially at the end of said low-temperature section of said heating cycle during said venting phase of said gas exchange period;

determining a difference between said value and said further value of said selected property of said metal oxide semiconductor by subtracting said further value measured close to said end of said low-temperature section of said heating cycle during said venting phase of said gas exchange period from said value measured close to said end of said low-temperature section of said heating cycle during said suction phase of said gas exchange period;

by means of said determined difference, detecting the presence and/or determining the concentration of said at least one reducing gas in said gas mixture to be investigated;

determining a difference between said maximum values of said selected property of said metal oxide semiconductor by subtracting the maximum value measured during said high-temperature section of said heating cycle during said suction phase of said gas exchange period from the maximum value measured during said high-temperature section of said heating cycle during said venting phase of said gas exchange period; and comparing said difference determined between said maximum values and said difference determined between said value and said further value in order to identify said at least one reducing gas in said gas mixture to be investigated.

59. The method as defined in claim 32, further including the steps of:

additionally measuring a further value of said selected property of said metal oxide semiconductor of said gas sensor substantially at the end of said low-temperature section of said heating cycle during said venting phase of said gas exchange period;

determining a difference between said value and said further value of said selected property of said metal oxide semiconductor by subtracting said further value measured close to said end of said low-temperature section of said heating cycle during said venting phase of said gas exchange period from said value measured close to said end of said low-temperature section of said heating cycle during said suction phase of said gas exchange period;

by means of said determined difference, detecting the presence and/or determining the concentration of said at least one reducing gas in said gas mixture to be investigated; and comparing said maximum value of said selected property of said metal oxide semiconductor and measured during said high-temperature section of said heating cycle during said suction phase of said gas exchange period with said determined difference in order to identify the nature of said at least one reducing gas in said gas mixture to be investigated.

60. The method as defined in claim 32, further including the steps of:

additionally measuring a further value of said selected property of said metal oxide semiconductor of said gas sensor substantially at the end of said low-temperature section of said heating cycle during said venting phase of said gas exchange period;

determining a difference between said measured value and said measured further value of said selected property of said metal oxide semiconductor by subtracting said further value measured close to said end of said low-temperature section of said heating cycle during said venting phase of said gas exchange period from said value measured close to said end of said low-temperature section of said heating cycle during said suction phase of said gas exchange period;

by means of said determined difference, detecting the presence and/or determining the concentration of said at least one reducing gas in said gas mixture to be investigated; and comparing said maximum value of said selected property of said metal oxide semiconductor and measured during said high-temperature section of said heating cycle during said venting phase of said gas exchange period with said determined difference in order to identify the nature of said at least one reducing gas in said gas mixture to be investigated.

61. The method as defined in claim 19, further including the steps of:

determining a difference between said maximum values of said selected property of said metal oxide semiconductor of said gas sensor by subtracting said maximum value measured during said high-temperature section of said heating cycle during said venting phase of said gas exchange period from said maximum value measured during said high-temperature section of said heating cycle during said suction phase of said gas exchange period;

by means of said determined difference, detecting the presence and/or determining the concentration of said at least one reducing gas in said gas mixture to be investigated;

additionally measuring a further value of said selected property of said metal oxide semiconductor of said gas sensor substantially at the end of said low-temperature section of said heating cycle during said venting phase of said gas exchange period; and comparing said difference between said value and said further value with said difference of said maximum values in order to identify the nature of said at least one reducing gas in said gas mixture to be investigated.

62. The method as defined in claim 19, further including the step of:

by means of said maximum value of said selected property of said metal oxide semiconductor and measured during said high-temperature section of said heating cycle during said suction phase of said gas exchange period, detecting the presence and/or determining the concentration of said at least one reducing gas in said gas mixture to be investigated;

additionally measuring a further value of said selected property of said metal oxide semiconductor substantially at the end of said low-temperature section of said heating cycle during said venting phase of said gas exchange period;

determining a difference between said value and said further value of said selected property of said metal oxide semiconductor by subtracting said further value measured close to said end of said low-temperature section of said heating cycle during said venting phase of said gas exchange period from said value measured close to said end of said low-temperature section of said heating cycle during said suction phase of said gas exchange period; and comparing said difference between said value and said further value with said maximum value in order to identify the nature of said at least one reducing gas in said gas mixture to be investigated.

63. The method as defined in claim 19, further including the steps of:

by means of said maximum value of said selected property of said metal oxide semiconductor of said gas sensor and measured during said high-temperature section of said heating cycle during said venting phase of said gas exchange period, detecting the presence and/or determining the concentration of said at least one reducing gas in said gas mixture to be investigated;

additionally measuring a further value of said selected property of said metal oxide semiconductor substantially at the end of said low-temperature section of said heating cycle during said venting phase of said gas exchange period;

determining a difference between said value and said further value of said selected property of said metal oxide semiconductor by subtracting said further value measured close to said end of said low-temperature section of said heating cycle during said venting phase of said gas exchange period from said value measured close to said end of said low-temperature section of said heating cycle during said suction phase of said gas exchange period; and comparing said difference between said value and said further value with said maximum value in order to identify the nature of said at least one reducing gas in said gas mixture to be investigated.

64. The method as defined in claim 32, further including the steps of:

determining a difference between said maximum values of said selected property of said metal oxide semiconductor of said gas sensor by subtracting said maximum value measured during said high-temperature section of said heating cycle during said venting phase of said gas exchange period from said maximum value measured during said high-temperature section of said heating cycle during said suction phase of said gas exchange period;

by means of said determined difference, detecting the presence and/or determining the concentration of said at least one reducing gas in said gas mixture to be investigated;

additionally measuring a further value of said selected property of said metal oxide semiconductor of said gas sensor substantially at the end of said low-temperature section of said heating cycle during said venting phase of said gas exchange period; and comparing said difference between said value and said further value with said difference of said maximum values in order to identify the nature of said at least one reducing gas in said gas mixture to be investigated.

65. The method as defined in claim 32, further including the step of:

by means of said maximum value of said selected property of said metal oxide semiconductor and measured during said high-temperature section of said heating cycle during said suction phase of said gas exchange period, detecting the presence and/or determining the concentration of said at least one reducing gas in said gas mixture to be investigated;

additionally measuring a further value of said selected property of said metal oxide semiconductor substantially at the end of said low-temperature section of said heating cycle during said venting phase of said gas exchange period;

determining a difference between said value and said further value of said selected property of said metal oxide semiconductor by subtracting said further value measured close to said end of said low-temperature section of said heating cycle during said venting phase of said gas exchange period from said value measured close to said end of said low-temperature section of said heating cycle during said suction phase of said gas exchange period; and comparing said difference between said value and said further value with said maximum value in order to identify the nature of said at least one reducing gas in said gas mixture to be investigated.

66. The method as defined in claim 32, further including the step of:

by means of said maximum value of said selected property of said metal oxide semiconductor of said gas sensor and measured during said high-temperature section of said heating cycle during said venting phase of said gas exchange period, detecting the presence and/or determining the concentration of said at least one reducing gas in said gas mixture to be investigated;

additionally measuring a further value of said selected property of said metal oxide semiconductor substantially at the end of said low-temperature section of said heating cycle during said venting phase of said gas exchange period;

determining a difference between said value and said further value of said selected property of said metal oxide semiconductor by subtracting said further value measured close to said end of said low-temperature section of said heating cycle during said venting phase of said gas exchange period from said value measured close to said end of said low-temperature section of said heating cycle during said suction phase of said gas exchange period; and comparing said difference between said value and said further value with said maximum value in order to identify the nature of said at least one reducing gas in said gas mixture to be investigated.

67. The method as defined in claim 19, further including the step of:

by means of said value of said selected property of said metal oxide semiconductor of said gas sensor and measured close to said end of said low-temperature section of said heating cycle during said suction phase of said gas exchange period, detecting the presence and/or determining the concentration of said at least one reducing gas in said gas mixture to be investigated.

68. The method as defined in claim 32, further including the step of:

by means of said value of said selected property of said metal oxide semiconductor of said gas sensor and measured close to said end of said low-temperature section of said heating cycle during said suction phase of said gas exchange period, detecting the presence and/or determining the concentration of said at least one reducing gas in said gas mixture to be investigated.

69. The method as defined in claim 19, further including the step of:

by means of either one of said maximum values measured of said selected property of said metal oxide semiconductor of said gas sensor measured during said high-temperature section of said heating cycle during either said suction phase or said venting phase of said gas exchange period, detecting the presence and/or determining the concentration of said at least one reducing gas in said gas mixture to be investigated.

70. The method as defined in claim 32, further including the step of:

by means of either one of said maximum values measured of said selected property of said metal oxide semiconductor of said gas sensor measured during said high-temperature section of said heating cycle during either said suction phase or said venting phase of said gas exchange period, detecting the presence and/or determining the concentration of said at least one reducing gas in said gas mixture to be investigated.

71. The method as defined in claim 67, further including the step of:

comparing said value of said selected property of said metal oxide semiconductor of said gas sensor and measured close to said end of said low-temperature section of said heating cycle during said suction phase of said gas exchange period, with either one of said maximum values of said selected property of said metal oxide semiconductor in said high-temperature section of said heating cycle during either one of said suction phase or of said venting phase of said gas exchange period in order to identify the nature of said at least one reducing gas in said gas mixture to be investigated.

72. The method as defined in claim 70, further including the step of:

comparing either one of said maximum values of said selected property of said metal oxide semiconductor of said gas sensor and measured in said high-temperature section of said heating cycle during either one of said suction phase or said venting phase of said gas exchange period, with said value of said selected property of said metal oxide semiconductor measured close to said end of said low-temperature heating cycle during said suction phase of said gas exchange period in order to identify the nature of said at least one reducing gas in said gas mixture to be investigated.

73. The method as defined in claim 1, further including the steps of:

selecting as said gas sensor a pellistor operating according to the principle of catalytic combustion;

selecting the electric conductivity of said pellistor as said selected property of said gas sensor;

said step of cyclically varying the temperature of said pellistor entails heating said pellistor through a heating cycle of a predetermined duration;

said step of cyclically exposing said pellistor to said gas mixture to be investigated and at least partially to said reference gas entails periodically exchanging the gas to which said pellistor is exposed using gas displacement means providing a gas exchange period of a predetermined duration which is substantially twice said predetermined duration of said heating cycle and which encompasses a suction phase during which said pellistor is exposed to said gas mixture to be investigated and a venting phase during which said pellistor is exposed to said reference gas;

maintaining said pellistor at a first temperature during a high-temperature section of said heating cycle during a first part of said suction phase of said gas exchange period;

maintaining said pellistor at a second temperature during a low-temperature section following said high-temperature section of said heating cycle during a second part of said suction phase of said gas exchange period;

maintaining said pellistor at a third temperature during a high-temperature section of said heating cycle during a first part of said venting phase of said gas exchange period;

maintaining said pellistor at a fourth temperature during a low-temperature section following said high-temperature section of said heating cycle during a second part of said venting phase of said gas exchange period;

measuring a first value of said electric conductivity of said pellistor substantially at the end of said high-temperature section of said heating cycle during said suction phase of said gas exchange period;

measuring a second value of said electric conductivity of said pellistor substantially at the end of said high-temperature section of said heating cycle during said venting phase of said gas exchange period;

measuring a third value of said electric conductivity of said pellistor substantially at the end of said low-temperature section of said heating cycle during said suction phase of said gas exchange period;

measuring a fourth value of said electric conductivity of said pellistor substantially at the end of said low-temperature section of said heating cycle during said venting phase of said gas exchange period;

forming a difference between said first and said second measured values of said electric conductivity of said pellistor, by subtracting said second measured value from said first measured value of said electric conductivity in order to detect the presence and/or to determine the concentration of said at least one reducing gas in said gas mixture to be investigated;

forming a difference between said third and said fourth measured values of said electric conductivity of said pellistor, by subtracting said third measured value from said fourth measured value of said electric conductivity in order to detect the presence and/or to determine the concentration of said at least one reducing gas in said gas mixture to be investigated; and comparing said difference determined between said first and second measured values of said electric conductivity in order to identify the nature of said at least one reducing gas in said gas mixture to be investigated.

74. The method as defined in claim 73, further including the step of:

selecting as said first and said third temperature a temperature which is higher than said second temperature and said fourth temperature, respectively, by at least 50° C.

75. The method as defined in claim 74, further including the step of:

selecting a temperature of substantially 450° C. as said first temperature and as said third temperature.

76. The method as defined in claim 73, further including the step of:

selecting as said second temperature and as said fourth temperature a temperature in the range of about 100° C. to about 650° C.

77. The method as defined in claim 76, further including the step of:

selecting a temperature substantially of 300° C. as said second temperature and as said fourth temperature.

78. The method as defined in claim 73, further including the steps of:

presetting a value of said concentration of said at least one reducing gas in said gas mixture to be investigated; and triggering an alarm whenever said preset concentration of said at least one reducing gas is exceeded.

79. The method as defined in claim 73, further including the step of:

simultaneously and continuously varying said predetermined duration of said gas exchange period and of said heating cycle in order to vary the sensitivity of said pellistor with respect to said at least one reducing gas.

80. The method as defined in claim 73, further including the step of:

simultaneously and stepwisely varying said predetermined duration of said gas exchange period and of said heating cycle in order to vary the sensitivity of said pellistor with respect to said at least one reducing gas.

81. An apparatus for detecting at least one reducing gas in a gas mixture to be investigated and comprising:

a gas detector defining a measuring chamber;

said measuring chamber communicating with a source of said gas mixture to be investigated;

said gas detector containing a gas sensor which comprises a metal oxide semiconductor possessing a selected property which is dependent upon the presence of said at least one reducing gas in said gas mixture to be investigated;

heating means for heating said gas sensor to a predetermined temperature;

a reference chamber connected to said measuring chamber and containing a reference gas which contains a smaller amount or none of said at least one reducing gas;

said reference chamber being closed towards the external atmosphere and being provided with gas displacement means;

a driver unit operatively associated with said gas displacement means;

said gas displacement means, during operation by said driver unit, cyclically exposing said gas sensor to said gas mixture to be investigated and at least partially to said reference gas;

an evaluation circuit arrangement; and said gas sensor being operatively connected to said evaluation circuit arrangement and generating output signals which are supplied to said evaluation circuit arrangement.

82. The apparatus as defined in claim 81, wherein:

said gas detector is arranged in said measuring chamber.

83. The apparatus as defined in claim 81, wherein:

said selected property of said metal oxide semiconductor of said gas sensor constitutes the electrical conductivity of said metal oxide semiconductor.

84. The apparatus as defined in claim 81, wherein:

said selected property of said metal oxide semiconductor is directly dependent upon the concentration of said at least one reducing gas in said gas mixture to be investigated.

85. The apparatus as defined in claim 81, wherein:

said heating means heating said gas sensor such as to cyclically vary the temperature of said gas sensor between a predetermined upper threshold value and a predetermined lower threshold value.

86. An apparatus for detecting at least one reducing gas in a gas mixture to be investigated and comprising:

a gas detector defining a measuring chamber;

said gas detector containing a gas sensor which comprises a metal oxide semiconductor possessing a selected property which is dependent upon the presence of said at least one reducing gas in said gas mixture to be investigated;

heating means for heating said gas sensor to a predetermined temperature;

a reference chamber connected to said measuring chamber;

said reference chamber being closed towards the external atmosphere and being provided with gas displacement means;

an evaluation circuit arrangement;

said gas sensor being operatively connected to said evaluation circuit arrangement and generating output signals which are supplied to said evaluation circuit arrangement; and said gas displacement means comprising an electromagnetically excitable membrane.

87. An apparatus for detecting at least one reducing gas in a gas mixture to be investigated and comprising:

a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacement means;
an evaluation circuit arrangement;
said gas sensor being operatively connected to said evaluation circuit arrangement and generating output signals which are supplied to said evaluation circuit arrangement; and
said gas displacement means comprising an electrostatically excitable membrane.

88. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacement means;
an evaluation circuit arrangement;
said gas sensor being operatively connected to said evaluation circuit arrangement and generating output signals which are supplied to said evaluation circuit arrangement; and
said gas displacement means comprising a piezoelectrically excitable membrane.

89. The apparatus as defined in claim 88, wherein:
said gas displacement means constitutes a piezo foil.

90. The apparatus as defined in claim 88, wherein:
said gas displacement means comprises a foil made of polyvinylidenedifluoride.

91. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacment means;
an evaluation circuit arrangement;
said gas sensor being operatively connected to said evaluation circuit arrangement and generating output signals which are supplied to said evaluation circuit arrangement; and
said gas displacement means comprising a dimorphic piezoelectric element.

92. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacement means;
an evaluation circuit arrangement;
said gas sensor being operatively connected to said evaluation circuit arrangement and generating output signals which are supplied to said evaluation circuit arrangement; and
said gas displacement means comprising a thermomechanically excitable membrane.

93. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacement means;
an evaluation circuit arrangement;
said gas sensor being operatively connected to said evaluation circuit arrangement and generating output signals which are supplied to said evaluation circuit arrangement; and
said gas displacement means comprising a bimetallic element.

94. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacement means;
an evaluation circuit arrangement;
said gas sensor being operatively connected to said evaluation circuit arrangement and generating output signals which are supplied to said evaluation circuit arrangement;
said gas displacement means comprising a silicon foil; and said silicon foil being obtained by means of a microlithographic process.

95. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacement means;
an evaluation circuit arrangement;
said gas sensor being operatively connected to said evaluation circuit arrangement and generating output signals which are supplied to said evaluation circuit arrangement;
said gas displacement means constituting a displaceable piston;
said displaceable piston, during a suction phase of its operation, drawing in said gas mixture to be investigated and passing said gas mixture through said gas sensor in a heated state thereof and practically passing said gas mixture over said heated gas sensor, and said displaceable piston thereafter forcing back the thus obtained gas mixture;
said gas sensor defining a surface;
said gas mixture to be investigated and present in said measuring chamber substantially completely contacting said surface of said gas sensor by means of said displacement of said displaceable piston in order to convert as far as possible said at least one reducing gas at said surface of said gas sensor and to pass, during a venting phase of the operation of said displaceable piston, a gas mixture which is substantially free of said at least one reducing gas along said gas sensor and through said measuring chamber, when said displaceable piston is forced back;
a microswitch;
two power sources operatively connected to said heating means and delivering predetermined different heating voltages; and
said microswitch being operated during each stroke of said displaceable piston such that said different heating voltages are alternatingly supplied from said two power sources to said heating means.

96. The apparatus as defined in claim 93, further including:
a clearance volume defined by all of the members of said apparatus through which said gas mixture to be investigated passes during operation of said gas displacement means and which possess a predetermined volume; and
said clearance volume being maintained at a minimum by providing a minimum predetermined volume of all of said members of said apparatus.

97. The apparatus as defined in claim 95, wherein:
said measuring chamber possesses a predetermined volume;
said reference chamber possesses a predetermined volume;
said predetermined volume of said measuring chamber and said predetermined volume of said reference chamber being matched to each such that during each said suction phase a first sample of said gas mixture to be investigated is drawn into said measuring chamber through said inlet opening thereof and that during each said venting phase at least a portion of said gas mixture to be investigated leaves said measuring chamber through said inlet opening thereof.

98. The apparatus as defined in claim 97, wherein:
the ratio of said predetermined volume of said measuring chamber to said predetermined volume of said reference chamber has a value in excess of 1:100.

99. The apparatus as defined in claim 98, wherein:
said ratio of said predetermined volume of said measuring chamber to said predetermined volume of said reference chamber has a value in excess of 1:1000.

100. The apparatus as defined in claim 95, wherein:
said ratio of said predetermined volume of said reference chamber to said predetermined volume of said measuring chamber is greater than 5:1;
said gas sensor possesses a predetermined volume;
said heating means possess a predetermined volume; and
the ratio of the sum of said predetermined volumes of said reference chamber and of said measuring chamber to the sum of said predetermined volumes of said gas sensor and of said heating means has a value of about 6:1.

101. The apparatus as defined in claim 95, further including:
a connecting aperture connecting said measuring chamber and said reference chamber; and
said measuring chamber, said reference chamber and said connecting aperture possessing substantially the same cross-sectional area.

102. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacement means;
an evaluation circuit arrangement;
said gas sensor being operatively connected to said evaluation circuit arrangement and generating output signals which are supplied to said evaluation circuit arrangement;
a clearance volume defined by all of the members of said apparatus through which said gas mixture to be investigated passes during operation of said gas displacement means and which possess a predetermined volume; and
said clearance volume being maintained at a minimum by providing a minimum predetermined volume of all of said members of said apparatus.

103. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacement means;
an evaluation circuit arrangement;
said gas sensor being operatively connected to said evaluation circuit arrangement and generating output signals which are supplied to said evaluation circuit arrangement;
said measuring chamber possessing a predetermined volume;
said reference chamber possessing a predetermined volume; and
said predetermined volume of said measuring chamber and said predetermined volume of said reference chamber being matched to each other such that during each said suction phase a first sample of said gas mixture to be investigated is drawn into said measuring chamber through said inlet opening thereof and that during each said venting phase at least a portion of said gas mixture to be investigated leaves said measuring chamber through said inlet opening thereof.

104. The apparatus as defined in claim 103, wherein:
the ratio of said predetermined volume of said measuring chamber to said predetermined volume of said reference chamber has a value in excess of 1:100.

105. The apparatus as defined in claim 104, wherein:
said ratio of said predetermined volume of said measuring chamber to said predetermined volume of said reference chamber has a value in excess of 1:1000.

106. The apparatus as defined in claim 103, wherein:
said ratio of said predetermined volume of said reference chamber to said predetermined volume of said measuring chamber is greater than 5:1;
said gas sensor possesses a predetermined volume;
said heating means possess a predtermined volume; and
the ratio of the sum of said predetermined volumes of said reference chamber and of said measuring chamber to the sum of said predetermined volumes of said gas sensor and of said heating means has a value of about 6:1.

107. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacement means;
an evaluation circuit arrangement;
said gas sensor being operatively connected to said evaluation circuit arrangement and generating output signals which are supplied to said evaluation circuit arrangement;
a thermally insulating support;
said measuing chamber comprising a block defining one side and constituting said metal oxide semicondutor, said heating means and said thermally insulating support;
said block and said heating means being conjointly arranged at said thermally insulating support;
electrodes mounted at said block; and
said reference chamber being arranged at said one side of said block.

108. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacement means;
an evaluation circuit arrangement;
said gas sensor being operatively connected to said evaluation circuit arrangement and generating output signals which are supplied to said evaluation circuit arrangement;
a connecting aperture connecting said measuring chamber and said reference chamber; and
said measuring chamber, said reference chamber and said connecting aperture possessing substantially the same cross-sectional area.

109. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamer being closed toward the external atmosphere and being provided with gas displacement means;
an evaluation circuit arrangement;
said gas sensor being operatively connected to said evaluation circuit arrangement and generating output signals which are supplied to said evaluation circuit arrangement;
an abutment provided in said reference chamber;
said gas displacement means of said reference chamber comprising an oscillatable membrane; and said oscillatable membrane sealing engaging said abutment during a venting phase of the operation of said gas displacement means.

110. The apparatus as defined in claim 109, wherein: said abutment is of substantially conical shape.

111. The apparatus as defined in claim 109, further including:
a protective membrane; and
said protective membrane being arranged in front of said oscillatable membrane of said gas displacement means.

112. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacement means;
an evaluation circuit arrangement;
said gas sensor being operatively connected to said evaluation circuit arrangement and generating output signals which are supplied to said evaluation circuit arrangement;
a regeneratable gas-adsorbing filter;
said gas-adsorbing filter being regeneratable by heating after predetermined time intervals; and
said regeneratable gas-adsorbing filter being located in said reference chamber.

113. The apparatus as defined in claim 112, wherein, said regeneratable gas-adsorbing filter being arranged in said reference chamber in front of said connecting aperture connecting said reference chamber and said measuring chamber.

114. The apparatus as defined in claim 112, further including:
a further regeneratable gas-adsorbing filter;
said further gas-adsorbing filter being regeneratable by heating after predetermined time intervals; and
said further regeneratable gas-adsorbing filter being arranged in front of said inlet opening of said measuring chamber.

115. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacement means;
an evaluation circuit arrangment;
said gas sensor being operatively connected to said evaluation circuit arrangement and generating output signals which are supplied to said evaluation circuit arrangement;
a regeneratable gas-adsorbing filter;
said gas-adsorbing filter being regeneratable by heating after predetermined time intervals; and
said further regeneratable gas-adsorbing filter being arranged in front of said inlet opening of said measuring chamber.

116. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heated means for heating said gas sensor to a predetermined temperature;
a reference chamber connected to said measuring chamber;
said reference chamber being closed towards the external atmosphere and being provided with gas displacement means;
an evaluation circuit arrangement;
said gas sensor being operatively connected to said evaluation circuit arrangement and generating output signals which are supplied to said evaluation circuit arrangement; and
a further gas sensor located in said reference chamber.

117. The apparatus as defined in claim 116, wherein: said firther gas sensor being responsive to water vapor and constituting a reference sensor.

118. An apparatus for detecting at least one reducing gas in a gas mixture to be investigated and comprising:
a gas detector defining a measuring chamber;
said gas detector containing a gas sensor which comprises a metal oxide semiconductor possessing a selected property which is dependent upon the presence of said at least one reducing gas in said gas mixture to be investigated;
heating means for heating said gas sensor to a predetermined temperature;
a reference chamber connected to said measuring chamber;
said reference chamber being closed towards the external atmosphere and being provided with gas displacement means;
an evaluation circuit arrangement;
said gas sensor being operatively connected to said evaluation circuit arrangement and generating output signals which are supplied to said evaluation circuit arrangement;
a capillary tube constituting said inlet opening of said measuring chamber; and
said capillary tube having a predetermined length and a predetermined internal diameter.

119. The apparatus as defined in claim 118, wherein: said predetermined length of said capillary tube has a value of at least 2 mm; and
said predetermined internal diameter of said capillary tube has a maximum value of 1 mm.

120. The apparatus as defined in claim 119, wherein: said predetermined internal diameter of said capillary tube has a value of about 0.3 mm.

121. An apparatus for detecting at least one reducing gas in a gas mixture to be investigated and comprising:
a gas detector defining a measuring chamber;

said gas detector containing a gas sensor which comprises a metal oxide semiconductor possessing a selected property which is dependent upon the presence of said at least one reducing gas in said gas mixture to be investigated;

heating means for heating said gas sensor to a predetermined temperature;

a reference chamber connected to said measuring chamber;

said reference chamber being closed towards the external atmosphere and being provided with gas displacement means;

an evaluation circuit arrangement;

said gas sensor being operatively connected to said evaluation circuit arrangement and generating output signals which are supplied to said evaluation circuit arrangement;

a wall defined by said gas detector and made of a gas-tight, thermally insulating material; and said gas sensor tightly engaging said wall of said meauring chamber.

* * * * *